(12) United States Patent
Alvaro et al.

(10) Patent No.: US 8,133,908 B2
(45) Date of Patent: Mar. 13, 2012

(54) HETEROARYL DERIVATIVES OF N-{[(1S,4S,6S)-3-(2-PYRIDINYLCARBONYL)-3-AZABICYCLO[4.1.0]HEPT-4-YL]METHYL}-2-AMINE

(75) Inventors: Giuseppe Alvaro, Verona (IT); David Amantini, Verona (IT); Emiliano Castiglioni, Verona (IT); Romano Di Fabio, Verona (IT); Francesca Pavone, Verona (IT)

(73) Assignee: Glaxo Group Limited, Greenford, Middlesex (GB)

( * ) Notice: Subject to any disclaimer, the term of this patent is extended or adjusted under 35 U.S.C. 154(b) by 0 days.

(21) Appl. No.: 12/627,283

(22) Filed: Nov. 30, 2009

(65) Prior Publication Data

US 2010/0168131 A1 Jul. 1, 2010

Related U.S. Application Data

(60) Provisional application No. 61/236,302, filed on Aug. 24, 2009, provisional application No. 61/119,118, filed on Dec. 2, 2008.

(51) Int. Cl.
*A61K 31/44* (2006.01)
(52) U.S. Cl. ........ 514/354; 544/333; 544/405; 546/112; 546/268.1; 548/255; 548/373.1
(58) Field of Classification Search .................. 514/354; 544/333, 405; 546/112, 268.1; 548/255, 548/373.1
See application file for complete search history.

(56) References Cited

U.S. PATENT DOCUMENTS

2010/0144760 A1 6/2010 Alvaro et al. ................. 514/256

FOREIGN PATENT DOCUMENTS

| WO | WO 99/09024 A1 | 2/1999 |
|---|---|---|
| WO | WO 99/58533 A1 | 11/1999 |
| WO | WO 00/47576 A1 | 8/2000 |
| WO | WO 00/47577 A1 | 8/2000 |
| WO | WO 00/47580 A2 | 8/2000 |
| WO | WO 01/96302 A1 | 12/2001 |
| WO | WO 02/44172 A1 | 6/2002 |
| WO | WO 02/89800 A2 | 11/2002 |
| WO | WO 03/002559 A2 | 1/2003 |
| WO | WO 03/002561 A1 | 1/2003 |
| WO | WO 03/032991 A1 | 4/2003 |
| WO | WO 03/037847 A1 | 5/2003 |
| WO | WO 03/041711 A1 | 5/2003 |
| WO | WO 05/118548 A1 | 12/2005 |
| WO | WO 08/038251 A2 | 4/2008 |
| WO | WO 09/003993 A1 | 1/2009 |
| WO | WO 09/003997 A1 | 1/2009 |
| WO | WO 09/124956 A1 | 10/2009 |

*Primary Examiner* — James O Wilson
*Assistant Examiner* — Douglas M Willis
(74) *Attorney, Agent, or Firm* — Kathryn A. Lutomski; John Lemanowicz

(57) ABSTRACT

Disclosed are N-{[(1S,4S,6S)-3-(2-pyridinylcarbonyl)-3-azabicyclo[4.1.0]hept-4-yl]methyl}-2-heteroarylamine derivatives having the following formula:

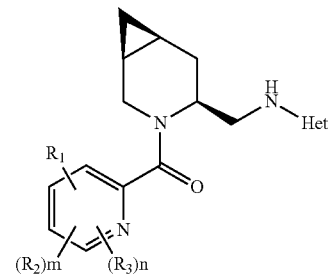

wherein m, n, Het, $R_1$, $R_2$ and $R_3$ are as defined herein, and their use as orexin antagonists.

16 Claims, No Drawings

HETEROARYL DERIVATIVES OF N-{[(1S,4S,6S)-3-(2-PYRIDINYLCARBONYL)-3-AZABICYCLO[4.1.0]HEPT-4-YL]METHYL}-2-AMINE

This application claims the benefit of U.S. Provisional Application Nos. 61/236,302, filed 24 Aug. 2009, and 61/119,118, filed 2 Dec. 2008.

BACKGROUND OF THE INVENTION

This invention relates to N-{[(1S,4S,6S)-3-(2-pyridinylcarbonyl)-3-azabicyclo[4.1.0]hept-4-yl]methyl}-2-heteroarylamine derivatives and their use as pharmaceuticals.

Many medically significant biological processes are mediated by proteins participating in signal transduction pathways that involve G-proteins and/or second messengers.

Polypeptides and polynucleotides encoding the human 7-transmembrane G-protein coupled neuropeptide receptor, orexin-1 (HFGAN72), have been identified and are disclosed in EP875565, EP875566 and WO 96/34877. Polypeptides and polynucleotides encoding a second human orexin receptor, orexin-2 (HFGANP), have been identified and are disclosed in EP893498.

Polypeptides and polynucleotides encoding polypeptides which are ligands for the orexin-1 receptor, e.g. orexin-A (Lig72A) are disclosed in EP849361.

The orexin ligand and receptor system has been well characterised since its discovery (see for example Sakurai, T. et al (1998) Cell, 92 pp 573 to 585; Smart et al (1999) British Journal of Pharmacology 128 pp 1 to 3; Willie et al (2001) Ann Rev. Neurosciences 24 pp 429 to 458; Sakurai (2007) Nature Reviews Neuroscience 8 pp 171 to 181; Ohno and Sakurai (2008) Front. Neuroendocrinology 29 pp 70 to 87). From these studies it has become clear that orexins and orexin receptors play a number of important physiological roles in mammals and open up the possibility of the development of new therapeutic treatments for a variety of diseases and disorders as described hereinbelow.

Experiments have shown that central administration of the ligand orexin-A stimulated food intake in freely-feeding rats during a 4 hour time period. This increase was approximately four-fold over control rats receiving vehicle. These data suggest that orexin-A may be an endogenous regulator of appetite (Sakurai, T. et al (1998) Cell, 92 pp 573 to 585; Peyron et al (1998) J. Neurosciences 18 pp 9996 to 10015; Willie et al (2001) Ann Rev. Neurosciences 24 pp 429 to 458). Therefore, antagonists of the orexin-A receptor(s) may be useful in the treatment of obesity and diabetes. In support of this it has been shown that orexin receptor antagonist SB334867 potently reduced hedonic eating in rats (White et al (2005) Peptides 26 pp 2231 to 2238) and also attenuated high-fat pellet self-administration in rats (Nair et al (2008) British Journal of Pharmacology, published online 28 Jan. 2008).

The search for new therapies to treat obesity and other eating disorders is an important challenge. According to WHO definitions a mean of 35% of subjects in 39 studies were overweight and a further 22% clinically obese in westernised societies. It has been estimated that 5.7% of all healthcare costs in the USA are a consequence of obesity. About 85% of Type 2 diabetics are obese. Diet and exercise are of value in all diabetics. The incidence of diagnosed diabetes in westernised countries is typically 5% and there are estimated to be an equal number undiagnosed. The incidence of obesity and Type 2 diabetes is rising, demonstrating the inadequacy of current treatments which may be either ineffective or have toxicity risks including cardiovascular effects. Treatment of diabetes with sulfonylureas or insulin can cause hypoglycaemia, whilst metformin causes GI side-effects. No drug treatment for Type 2 diabetes has been shown to reduce the long-term complications of the disease. Insulin sensitisers will be useful for many diabetics, however they do not have an anti-obesity effect.

As well as having a role in food intake, the orexin system is also involved in sleep and wakefulness. Rat sleep/EEG studies have shown that central administration of orexin-A, an agonist of the orexin receptors, causes a dose-related increase in arousal, largely at the expense of a reduction in paradoxical sleep and slow wave sleep 2, when administered at the onset of the normal sleep period (Hagan et al (1999) Proc. Natl. Acad. Sci. 96 pp 10911 to 10916). The role of the orexin system in sleep and wakefulness is now well established (Sakurai (2007) Nature Reviews Neuroscience 8 pp 171 to 181; Ohno and Sakurai (2008) Front. Neuroendocrinology 29 pp 70 to 87; Chemelli et al (1999) Cell 98 pp 437 to 451; Lee et al (2005) J. Neuroscience 25 pp 6716 to 6720; Piper et al (2000) European J Neuroscience 12 pp 726-730 and Smart and Jerman (2002) Pharmacology and Therapeutics 94 pp 51 to 61). Antagonists of the orexin receptors may therefore be useful in the treatment of sleep disorders including insomnia. Studies with orexin receptor antagonists, for example SB334867, in rats (see for example Smith et al (2003) Neuroscience Letters 341 pp 256 to 258) and more recently dogs and humans (Brisbare-Roch et al (2007) Nature Medicine 13(2) pp 150 to 155) further support this.

In addition, recent studies have suggested a role for orexin antagonists in the treatment of motivational disorders, such as disorders related to reward seeking behaviours for example drug addiction and substance abuse (Borgland et al (2006) Neuron 49(4) pp 589-601; Boutrel et al (2005) Proc. Natl. Acad. Sci. 102(52) pp 19168 to 19173; Harris et al (2005) Nature 437 pp 556 to 559).

International Patent Applications WO99/09024, WO99/58533, WO00/47577 and WO00/47580 disclose phenyl urea derivatives and WO00/47576 discloses quinolinyl cinnamide derivatives as orexin receptor antagonists. WO05/118548 discloses substituted 1,2,3,4-tetrahydroisoquinoline derivatives as orexin antagonists.

WO01/96302, WO02/44172, WO02/89800, WO03/002559, WO03/002561, WO03/032991, WO03/037847, WO03/041711, WO08/038,251, WO09/003,993, WO09/003,997 and WO09/124,956 all disclose cyclic amine derivatives.

WO08/038,251 discloses 3-aza-bicyclo[3.1.0]hexane derivatives as orexin antagonists.

SUMMARY OF THE INVENTION

We have now found that N-{[(1S,4S,6S)-3-(2-pyridinylcarbonyl)-3-azabicyclo[4.1.0]hept-4-yl]methyl}-2-heteroarylamine derivatives have beneficial properties including, for example, high potency, good brain penetration and good bioavailability. Such properties make these N-{[(1S,4S,6S)-3-(2-pyridinylcarbonyl)-3-azabicyclo[4.1.0]hept-4-yl]methyl}-2-heteroarylamine derivatives very attractive as potential pharmaceutical agents which may be useful in the prevention or treatment of obesity, including obesity observed in Type 2 (non-insulin-dependent) diabetes patients, sleep disorders, anxiety, depression, schizophrenia, drug dependency or compulsive behaviour. Additionally these compounds may be useful in the treatment of stroke, particularly ischemic or haemorrhagic stroke, and/or blocking the emetic response, i.e. useful in the treatment of nausea and vomiting.

Accordingly the present invention provides a compound of formula (I)

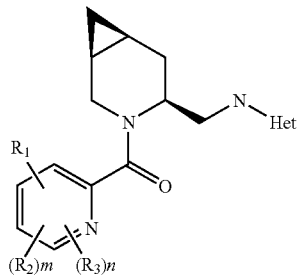

wherein:

Het is a heteroaryl group selected from the group consisting of pyridinyl, pyrimidinyl, pyridazinyl or pyrazinyl, said heteroaryl group being optionally substituted with 1, 2 or 3 substituents independently selected from the group consisting of: $C_{1-4}$alkyl, halo, $C_{1-4}$alkoxy, halo$C_{1-4}$alkoxy and cyano;

$R_1$ is $C_{1-4}$alkyl, halo, $C_{1-4}$alkoxy, halo$C_{1-4}$alkyl, halo$C_{1-4}$alkoxy, cyano, $C_{1-4}$alkylSO$_2$, $C_{3-8}$ cycloalkylSO$_2$, $C_{3-8}$cycloalkylCH$_2$SO$_2$, phenyl or a 5 or 6 membered heterocyclyl group containing 1, 2 or 3 atoms selected from N, O or S, which phenyl or heterocyclyl group is optionally substituted with $C_{1-4}$alkyl, halo, $C_{1-4}$alkoxy, halo$C_{1-4}$alkyl, halo$C_{1-4}$alkoxy or cyano;

$R_2$ is $C_{1-4}$alkyl, halo, $C_{1-4}$alkoxy, halo$C_{1-4}$alkoxy, cyano, phenyl or a 5 or 6 membered heterocyclyl group containing 1, 2 or 3 atoms selected from N, O or S, which phenyl or heterocyclyl group is optionally substituted with $C_{1-4}$alkyl, halo, $C_{1-4}$alkoxy, halo$C_{1-4}$alkyl, halo$C_{1-4}$alkoxy or cyano;

$R_3$ is $C_{1-4}$alkyl, halo, $C_{1-4}$alkoxy, halo$C_{1-4}$alkyl, halo$C_{1-4}$alkoxy or cyano;

m is 0 or 1; and n is 0 or 1;

or a pharmaceutically acceptable salt thereof.

DETAILED DESCRIPTION OF THE INVENTION

In one embodiment Het is a heteroaryl group selected from the group consisting of pyridinyl, pyrimidinyl, pyridazinyl or pyrazinyl, said heteroaryl group being optionally substituted with 1, 2 or 3 substituents independently selected from the group consisting of:

$C_{1-4}$alkyl, halo, $C_{1-4}$alkoxy, halo$C_{1-4}$alkyl, halo$C_{1-4}$alkoxy and cyano;

$R_1$ is $C_{1-4}$alkyl, halo, $C_{1-4}$alkoxy, halo$C_{1-4}$alkyl, halo$C_{1-4}$alkoxy, cyano, $C_{1-4}$alkylSO$_2$, $C_{3-8}$ cycloalkylSO$_2$, $C_{3-8}$cycloalkylCH$_2$SO$_2$, phenyl or a 5 or 6 membered heterocyclyl group containing 1, 2 or 3 atoms selected from N, O or S, which phenyl or heterocyclyl group is optionally substituted with 1 or 2 groups selected from $C_{1-4}$alkyl, halo, $C_{1-4}$alkoxy, halo$C_{1-4}$alkyl, halo$C_{1-4}$alkoxy or cyano;

$R_2$ is $C_{1-4}$alkyl, halo, $C_{1-4}$alkoxy, halo$C_{1-4}$alkyl, halo$C_{1-4}$alkoxy, cyano, phenyl or a 5 or 6 membered heterocyclyl group containing 1, 2 or 3 atoms selected from N, O or S, which phenyl or heterocyclyl group is optionally substituted with 1 or 2 groups selected from $C_{1-4}$alkyl, halo, $C_{1-4}$alkoxy, halo$C_{1-4}$alkyl, halo$C_{1-4}$alkoxy or cyano;

$R_3$ is $C_{1-4}$alkyl, halo, $C_{1-4}$alkoxy, halo$C_{1-4}$alkyl, halo$C_{1-4}$alkoxy or cyano;

m is 0 or 1; and n is 0 or 1;

or a pharmaceutically acceptable salt thereof.

In one embodiment Het is substituted with halo$C_{1-4}$alkyl.

In another embodiment Het is substituted with trifluoromethyl.

In one embodiment Het is pyridinyl.

In one embodiment Het is pyridazinyl.

In one embodiment Het is pyrazinyl.

In one embodiment Het is pyrimidinyl.

In another embodiment Het is pyridinyl substituted with trifluoromethyl or cyano.

In another embodiment Het is pyrimidinyl substituted with 1 or 2 CH$_3$ groups.

In one embodiment m and n are both 0.

In one embodiment m is 1 and n is 0.

In one embodiment $R_1$ is CH$_3$.

In another embodiment $R_1$ is CH$_3$ and m and n are both 0.

In one embodiment $R_2$ is methoxy, ethoxy or propoxy.

In another embodiment $R_2$ is phenyl, pyrimidinyl, oxadiazolyl, oxazolyl, isoxazolyl, thiazolyl, triazolyl, imidazolyl, pyrazolinyl, pyridazinyl, pyrazinyl or pyridinyl.

In a further embodiment $R_2$ is phenyl substituted with fluoro.

In a still further embodiment $R_2$ is oxadiazolyl, oxazolyl or thiazolyl substituted with methyl.

In a still further embodiment $R_2$ is oxadiazolyl, oxazolyl or thiazolyl substituted with ethyl.

In one embodiment m is 1, n is 0, $R_1$ is CH$_3$ and $R_2$ is methoxy, ethoxy or propoxy.

In one embodiment Het is pyridinyl, m is 1, n is 0, $R_1$ is CH$_3$, $R_2$ is methoxy, ethoxy or propoxy.

In another embodiment Het is pyridinyl substituted with trifluoromethyl or cyano, m is 1, n is 0, $R_1$ is CH$_3$ and $R_2$ is methoxy, ethoxy or propoxy.

In one embodiment Het is pyrimidinyl, m is 1, n is 0, $R_1$ is CH$_3$ and $R_2$ is methoxy, ethoxy or propoxy.

In another embodiment Het is pyrimidinyl substituted with 1 or 2 CH$_3$ groups, m is 1, n is 0, $R_1$ is CH$_3$ and $R_2$ is methoxy, ethoxy or propoxy.

In a further embodiment Het is pyridinyl substituted with halo$C_{1-4}$alkyl; $R_1$ is $C_{1-4}$alkyl; $R_2$ is ethoxy, propoxy or pyrimidinyl; m is 1; and n is 0.

In a still further embodiment Het is pyridinyl substituted with trifluoromethyl; $R_1$ is methyl; $R_2$ is ethoxy, propoxy or pyrimidinyl; m is 1; and n is 0.

In one embodiment Het is pyridinyl substituted with trifluoromethyl, m is 1, n is 0, $R_1$ is CH$_3$ and $R_2$ is pyrimidinyl.

In one embodiment Het is pyrazinyl substituted with trifluoromethyl, m is 1, n is 0, $R_1$ is CH$_3$ and $R_2$ is pyrimidinyl, or a pharmaceutically acceptable salt thereof.

In one embodiment Het is pyridinyl optionally substituted with 1, 2 or 3 substituents independently selected from the group consisting of: $C_{1-4}$alkyl, halo, $C_{1-4}$alkoxy, halo$C_{1-4}$alkyl, halo$C_{1-4}$alkoxy and cyano; $R_1$ is $C_{1-4}$alkyl, halo, $C_{1-4}$alkoxy, halo$C_{1-4}$alkyl, halo$C_{1-4}$alkoxy, cyano, $C_{1-4}$alkylSO$_2$, $C_{3-8}$cycloalkylSO$_2$, $C_{3-8}$cycloalkylCH$_2$SO$_2$; $R_2$ is $C_{1-4}$alkyl, halo, $C_{1-4}$alkoxy, halo$C_{1-4}$alkyl, halo$C_{1-4}$alkoxy, cyano, phenyl or a 5 or 6 membered heterocyclyl group containing 1, 2 or 3 atoms selected from N, O or S, which phenyl or heterocyclyl group is optionally substituted with $C_{1-4}$alkyl, halo, $C_{1-4}$alkoxy, halo$C_{1-4}$alkyl, halo$C_{1-4}$alkoxy or cyano; m is 1; and n is 0.

In another embodiment Het is pyridinyl substituted with 1 substituent selected from the group consisting of: $C_{1-4}$alkyl, halo, $C_{1-4}$alkoxy, halo$C_{1-4}$alkyl, halo$C_{1-4}$alkoxy and cyano; $R_1$ is $C_{1-4}$alkyl, halo, $C_{1-4}$alkoxy, halo$C_{1-4}$alkyl, halo$C_{1-4}$alkoxy, cyano; $R_2$ is $C_{1-4}$alkoxy or a 5 or 6 membered heterocyclyl group containing 1, 2 or 3 atoms selected from N, O or S, which heterocyclyl group is optionally substituted with $C_{1-4}$alkyl, halo, $C_{1-4}$alkoxy, halo$C_{1-4}$alkyl, halo$C_{1-4}$alkoxy or cyano; m is 1; and n is 0.

In one embodiment the invention provides the compound of formula (I) selected from the group consisting of:

N-[((1S,4S,6S)-3-{[6-methyl-3-(propyloxy)-2-pyridinyl] carbonyl}-3-azabicyclo[4.1.0]hept-4-yl)methyl]-5-(trifluoromethyl)-2-pyridinamine;

N-[((1S,4S,6S)-3-{[3-(ethyloxy)-6-methyl-2-pyridinyl]carbonyl}-3-azabicyclo[4.1.0]hept-4-yl)methyl]-5-(trifluoromethyl)-2-pyridinamine;

N-[((1S,4S,6S)-3-{[6-methyl-3-(2-pyrimidinyl)-2-pyridinyl]carbonyl}-3-azabicyclo[4.1.0]hept-4-yl)methyl]-5-(trifluoromethyl)-2-pyridinamine;

N-[((1S,4S,6S)-3-{[6-methyl-3-(2-pyrimidinyl)-2-pyridinyl]carbonyl}-3-azabicyclo[4.1.0]hept-4-yl)methyl]-5-(trifluoromethyl)-2-pyrazinamine;

N-[((1S,4S,6S)-3-{[6-methyl-3-(1H-pyrazol-1-yl)-2-pyridinyl]carbonyl}-3-azabicyclo[4.1.0]hept-4-yl)methyl]-5-(trifluoromethyl)-2-pyrazinamine; and N-[((1S,4S,6S)-3-{[6-methyl-3-(2H-1,2,3-triazol-2-yl)-2-pyridinyl]carbonyl}-3-azabicyclo[4.1.0]hept-4-yl)methyl]-5-(trifluoromethyl)-2-pyrazinamine;

or a pharmaceutically acceptable salt thereof.

The Het group (pyridinyl, pyrimidinyl, pyridazinyl or pyrazinyl) may be attached to the aminomethyl linker by means of a bond between the nitrogen atom in said linker and any carbon or suitable nitrogen atom in said pyridinyl, pyrimidinyl, pyridazinyl or pyrazinyl ring. Preferably the Het group is attached to the linker by means of a bond between the nitrogen atom in the linker and a carbon atom in the Het group ring.

When $R_1$ or $R_2$ is a heterocyclic group it can be any 5 or 6 membered heterocyclyl group containing 1, 2 or 3 atoms selected from N, O or S. Examples of such heterocyclic groups include pyrimidinyl, oxadiazolyl, oxazolyl, isoxazolyl, thiazolyl, triazolyl, imidazolyl, pyrazolinyl, pyridazinyl, pyrazinyl, pyridinyl, furanyl, thienyl, pyrrolyl, thiadiazolyl, triazinyl and isothiazolyl.

When $R_1$ or $R_2$ is a heterocyclic group, said group may be attached to the pyridyl ring by means of a bond between a carbon atom of said pyridyl ring and a carbon or a suitable heteroatom of the heterocyclic group. For example where $R_2$ is a triazolyl group the attachment to the pyridyl ring may be by means of a bond between a carbon atom on the pyridyl ring and a) one of the two carbon atoms or b) one of the three nitrogen atoms of the triazolyl group.

When the compound contains a $C_{1-4}$alkyl group, whether alone or forming part of a larger group, e.g. $C_{1-4}$alkoxy, the alkyl group may be straight chain, branched or cyclic, or combinations thereof. Examples of $C_{1-4}$alkyl are methyl or ethyl.

Examples of halo$C_{1-4}$alkyl include trifluoromethyl (i.e. —$CF_3$).

Examples of $C_{1-4}$alkoxy include methoxy and ethoxy.

Examples of halo$C_{1-4}$alkoxy include trifluoromethoxy (i.e. —$OCF_3$).

Halogen or "halo" (when used, for example, in halo$C_{1-4}$ alkyl) means fluoro, chloro, bromo or iodo.

It is to be understood that the present invention covers all combinations of particularised groups and substituents described herein above.

It will be appreciated that for use in medicine the salts of the compounds of formula (I) should be pharmaceutically acceptable. Suitable pharmaceutically acceptable salts will be apparent to those skilled in the art. Pharmaceutically acceptable salts include those described by Berge, Bighley and Monkhouse J. Pharm. Sci (1977) 66, pp 1-19. Such pharmaceutically acceptable salts include acid addition salts formed with inorganic acids e.g. hydrochloric, hydrobromic, sulphuric, nitric or phosphoric acid and organic acids e.g. succinic, maleic, acetic, fumaric, citric, tartaric, benzoic, p-toluenesulfonic, methanesulfonic or naphthalenesulfonic acid. Other salts e.g. oxalates or formates, may be used, for example in the isolation of compounds of formula (I) and represent another aspect of this invention.

Certain of the compounds of formula (I) may form acid addition salts with one or more equivalents of the acid. The present invention includes within its scope all possible stoichiometric and non-stoichiometric forms.

The compounds of formula (I) may be prepared in crystalline or non-crystalline form and, if crystalline, may optionally be solvated, eg. as the hydrate. This invention includes within its scope stoichiometric solvates (eg. hydrates) as well as compounds containing variable amounts of solvent (eg. water).

As used herein "pharmaceutically acceptable derivative" includes any pharmaceutically acceptable ester or salt of such ester of a compound of formula (I) which, upon administration to the recipient is capable of providing (directly or indirectly) a compound of formula (I) or an active metabolite or residue thereof.

The stereogenic centres of the compounds of formula (I) are in a cis (1S,4S,6S)-configuration. The invention also extends to any tautomeric forms or mixtures thereof.

The subject invention also includes isotopically-labeled compounds which are identical to those recited in formula (I) but for the fact that one or more atoms are replaced by an atom having an atomic mass or mass number different from the atomic mass or mass number most commonly found in nature. Examples of isotopes that can be incorporated into compounds of the invention include isotopes of hydrogen, carbon, nitrogen, oxygen, fluorine, iodine and chlorine such as $^3H$, $^{11}C$, $^{14}C$, $^{18}F$, $^{123}I$ or $^{125}I$.

Compounds of the present invention and pharmaceutically acceptable salts of said compounds that contain the aforementioned isotopes and/or other isotopes of other atoms are within the scope of the present invention. Isotopically labeled compounds of the present invention, for example those into which radioactive isotopes such as $^3H$ or $^{14}C$ have been incorporated, are useful in drug and/or substrate tissue distribution assays. Tritiated, ie. $^3H$, and carbon-14, ie. $^{14}C$, isotopes are particularly preferred for their ease of preparation and detectability. $^{11}C$ and $^{18}F$ isotopes are particularly useful in PET (positron emission tomography).

Since the compounds of formula (I) are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions.

According to a further aspect of the present invention there is provided a process for the preparation of compounds of formula (I) and derivatives thereof. The following schemes detail some synthetic routes to compounds of the invention. In the following schemes reactive groups can be protected with protecting groups and deprotected according to well established techniques.

Schemes

According to a further aspect of the invention there is provided a process for the preparation of compounds of formula (I) or salts thereof. The following schemes are examples of synthetic schemes that may be used to synthesise the compounds of the invention.

Scheme 1
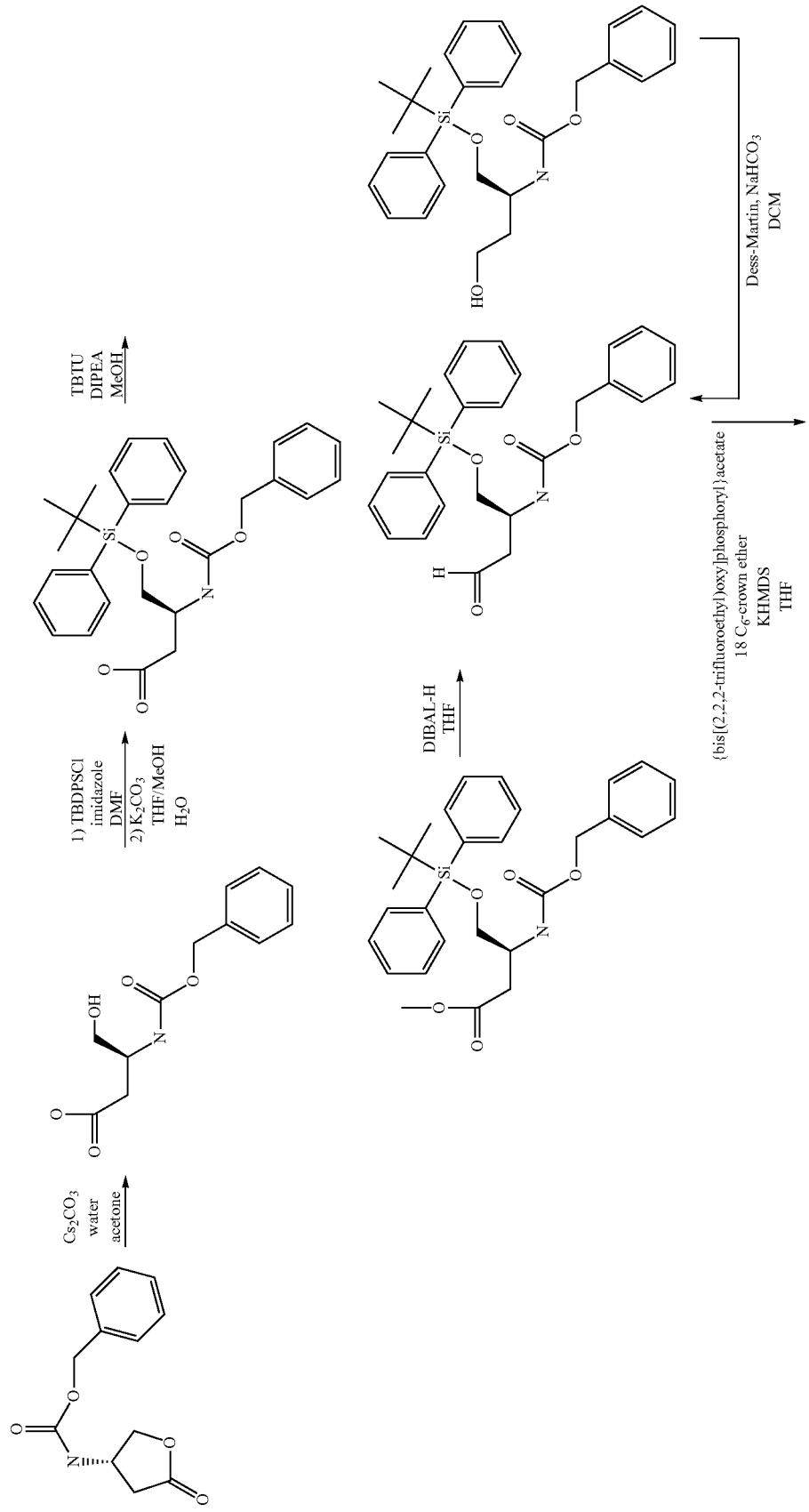

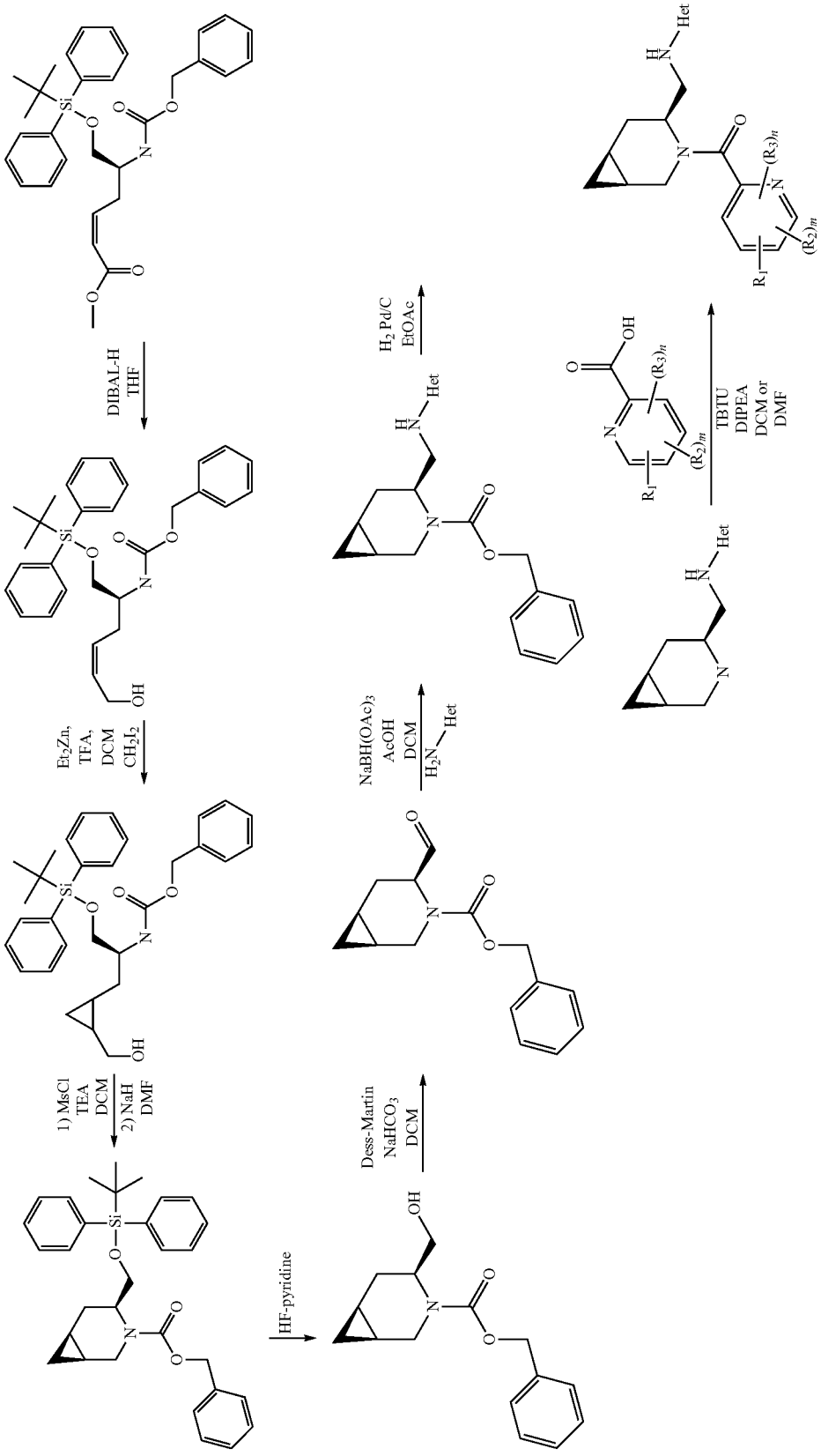

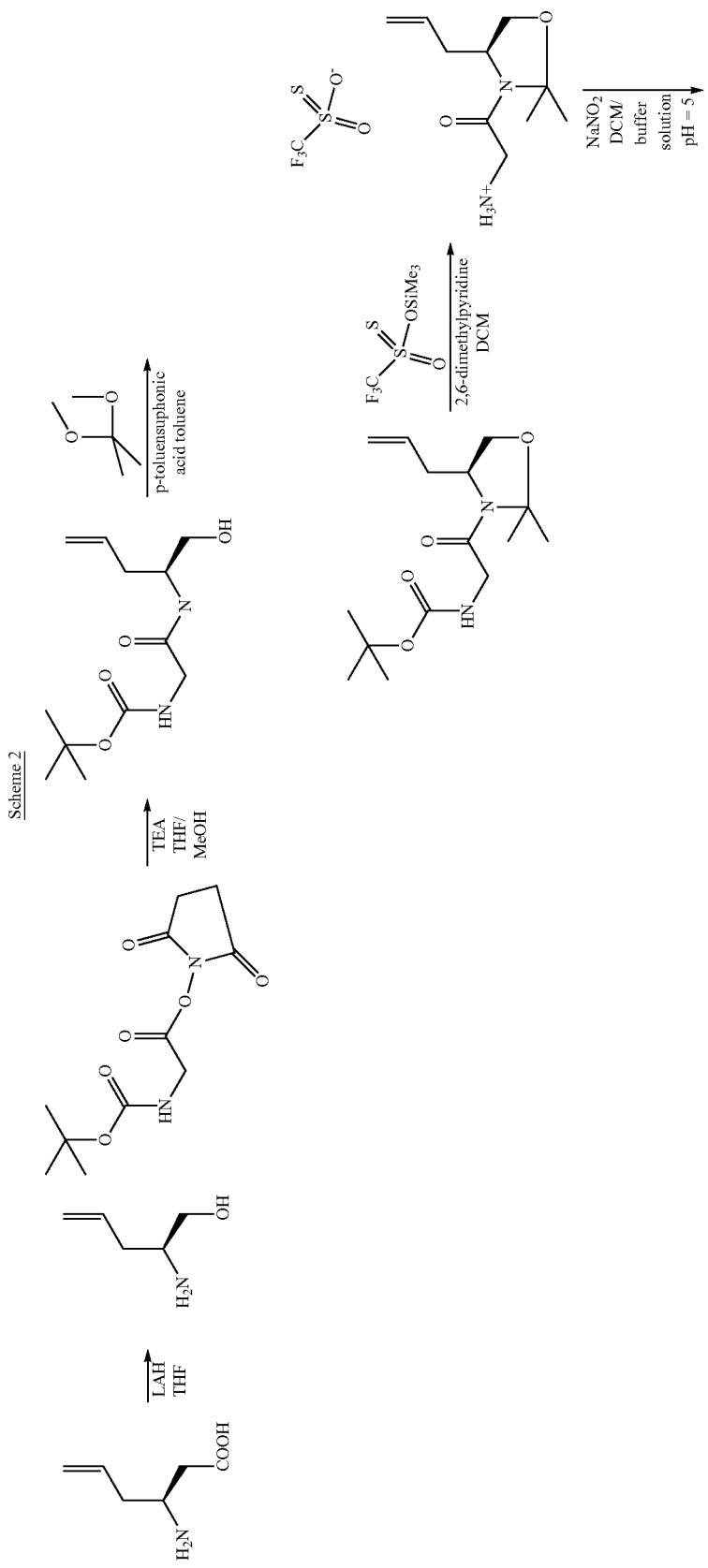

-continued
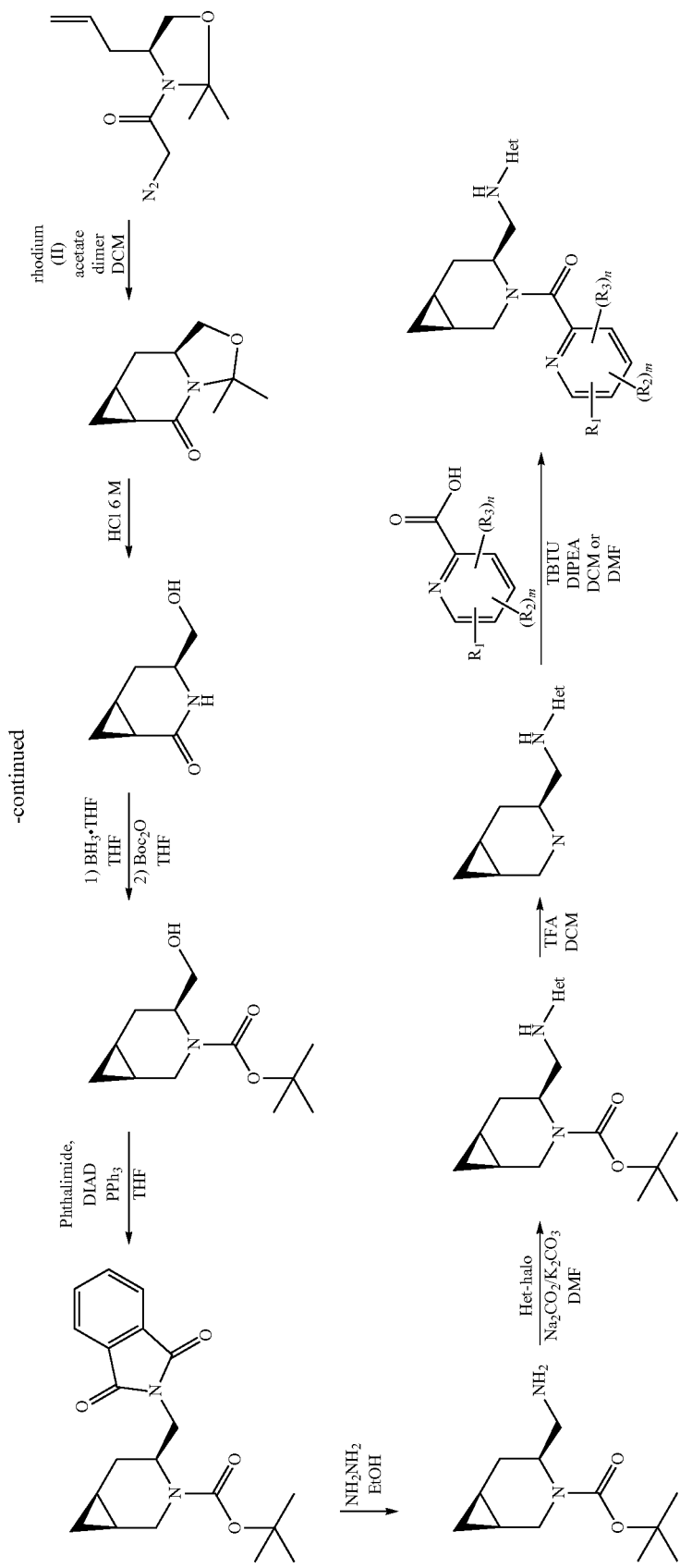

In the schemes Het, $R_1$, $R_2$, $R_3$, m and n have the meanings given in formula (I). It will be understood by those skilled in the art that certain compounds of the invention can be converted into other compounds of the invention according to standard chemical methods.

The starting materials for use in the scheme are commercially available, known in the literature or can be prepared by known methods. Phenylmethyl [(3S)-5-oxotetrahydro-3-furanyl]carbamate (available from Sigma-Aldrich #419249), (2S)-2-amino-4-pentenoic acid (available from Sigma-Aldrich #285013) and 2,5-dioxo-1-pyrrolidinyl N-{[(1,1-dimethylethyl)oxy]carbonyl}glycinate (available from Sigma-Aldrich #15423).

Pharmaceutically acceptable salts may be prepared conventionally by reaction with the appropriate acid or acid derivative.

The present invention provides compounds of formula (I) or a pharmaceutically acceptable salt thereof for use in human or veterinary medicine.

The compounds of formula (I) or their pharmaceutically acceptable salts may be of use for the treatment or prophylaxis of a disease or disorder where an antagonist of a human orexin receptor is required.

Compounds of formula (I) or their pharmaceutically acceptable salts may be of use for the treatment or prophylaxis of sleep disorders selected from the group consisting of Dyssomnias such as Primary Insomnia (307.42), Primary Hypersomnia (307.44), Narcolepsy (347), Breathing-Related Sleep Disorders (780.59), Circadian Rhythm Sleep Disorder (307.45) and Dyssomnia Not Otherwise Specified (307.47); primary sleep disorders such as Parasomnias such as Nightmare Disorder (307.47), Sleep Terror Disorder (307.46), Sleepwalking Disorder (307.46) and Parasomnia Not Otherwise Specified (307.47); Sleep Disorders Related to Another Mental Disorder such as Insomnia Related to Another Mental Disorder (307.42) and Hypersomnia Related to Another Mental Disorder (307.44); Sleep Disorder Due to a General Medical Condition, in particular sleep disturbances associated with such diseases as neurological disorders, neuropathic pain, restless leg syndrome, heart and lung diseases; and Substance-Induced Sleep Disorder including the subtypes Insomnia Type, Hypersomnia Type, Parasomnia Type and Mixed Type; Sleep Apnea and Jet-Lag Syndrome.

In one embodiment compounds of formula (I) or their pharmaceutically acceptable salts may be of use for the treatment or prophylaxis of Primary Insomnia (307.42), Circadian Rhythm Sleep Disorder (307.45) and Dyssomnia Not Otherwise Specified (307.47), Sleep Disorders Related to Another Mental Disorder such as Insomnia Related to Another Mental Disorder (307.42) and Sleep Disorder Due to a General Medical Condition, in particular sleep disturbances associated with such diseases as neurological disorders, neuropathic pain, restless leg syndrome, heart and lung diseases; and Substance-Induced Sleep Disorder including the subtypes Insomnia Type, Hypersomnia Type, Parasomnia Type and Mixed Type.

In addition the compounds of formula (I) or their pharmaceutically acceptable salts may be of use for the treatment or prophylaxis of depression and mood disorders including Major Depressive Episode, Manic Episode, Mixed Episode and Hypomanic Episode; Depressive Disorders including Major Depressive Disorder, Dysthymic Disorder (300.4), Depressive Disorder Not Otherwise Specified (311); Bipolar Disorders including Bipolar I Disorder, Bipolar II Disorder (Recurrent Major Depressive Episodes with Hypomanic Episodes) (296.89), Cyclothymic Disorder (301.13) and Bipolar Disorder Not Otherwise Specified (296.80); Other Mood Disorders including Mood Disorder Due to a General Medical Condition (293.83) which includes the subtypes With Depressive Features, With Major Depressive-like Episode, With Manic Features and With Mixed Features), Substance-Induced Mood Disorder (including the subtypes With Depressive Features, With Manic Features and With Mixed Features) and Mood Disorder Not Otherwise Specified (296.90).

Further, the compounds of formula (I) or their pharmaceutically acceptable salts may be of use for the treatment or prophylaxis of anxiety disorders including Panic Attack; Panic Disorder including Panic Disorder without Agoraphobia (300.01) and Panic Disorder with Agoraphobia (300.21); Agoraphobia; Agoraphobia Without History of Panic Disorder (300.22), Specific Phobia (300.29, formerly Simple Phobia) including the subtypes Animal Type, Natural Environment Type, Blood-Injection-Injury Type, Situational Type and Other Type), Social Phobia (Social Anxiety Disorder, 300.23), Obsessive-Compulsive Disorder (300.3), Posttraumatic Stress Disorder (309.81), Acute Stress Disorder (308.3), Generalized Anxiety Disorder (300.02), Anxiety Disorder Due to a General Medical Condition (293.84), Substance-Induced Anxiety Disorder, Separation Anxiety Disorder (309.21), Adjustment Disorders with Anxiety (309.24) and Anxiety Disorder Not Otherwise Specified (300.00).

In addition the compounds of formula (I) or their pharmaceutically acceptable salts may be of use for the treatment or prophylaxis of substance-related disorders including Substance Use Disorders such as Substance Dependence, Substance Craving and Substance Abuse; Substance-Induced Disorders such as Substance Intoxication, Substance Withdrawal, Substance-Induced Delirium, Substance-Induced Persisting Dementia, Substance-Induced Persisting Amnestic Disorder, Substance-Induced Psychotic Disorder, Substance-Induced Mood Disorder, Substance-Induced Anxiety Disorder, Substance-Induced Sexual Dysfunction, Substance-Induced Sleep Disorder and Hallucinogen Persisting Perception Disorder (Flashbacks); Alcohol-Related Disorders such as Alcohol Dependence (303.90), Alcohol Abuse (305.00), Alcohol Intoxication (303.00), Alcohol Withdrawal (291.81), Alcohol Intoxication Delirium, Alcohol Withdrawal Delirium, Alcohol-Induced Persisting Dementia, Alcohol-Induced Persisting Amnestic Disorder, Alcohol-Induced Psychotic Disorder, Alcohol-Induced Mood Disorder, Alcohol-Induced Anxiety Disorder, Alcohol-Induced Sexual Dysfunction, Alcohol-Induced Sleep Disorder and Alcohol-Related Disorder Not Otherwise Specified (291.9); Amphetamine (or Amphetamine-Like)-Related Disorders such as Amphetamine Dependence (304.40), Amphetamine Abuse (305.70), Amphetamine Intoxication (292.89), Amphetamine Withdrawal (292.0), Amphetamine Intoxication Delirium, Amphetamine Induced Psychotic Disorder, Amphetamine-Induced Mood Disorder, Amphetamine-Induced Anxiety Disorder, Amphetamine-Induced Sexual Dysfunction, Amphetamine-Induced Sleep Disorder and Amphetamine-Related Disorder Not Otherwise Specified (292.9); Caffeine Related Disorders such as Caffeine Intoxication (305.90), Caffeine-Induced Anxiety Disorder, Caffeine-Induced Sleep Disorder and Caffeine-Related Disorder Not Otherwise Specified (292.9); *Cannabis*-Related Disorders such as *Cannabis* Dependence (304.30), *Cannabis* Abuse (305.20), *Cannabis* Intoxication (292.89), *Cannabis* Intoxication Delirium, *Cannabis*-Induced Psychotic Disorder, *Cannabis*-Induced Anxiety Disorder and *Cannabis*-Related Disorder Not Otherwise Specified (292.9); Cocaine-Related Disorders such as Cocaine Dependence (304.20), Cocaine Abuse (305.60), Cocaine Intoxication (292.89), Cocaine Withdrawal (292.0), Cocaine Intoxication Delirium, Cocaine-Induced Psychotic Disorder, Cocaine-Induced Mood Disorder, Cocaine-Induced Anxiety Disorder, Cocaine-Induced Sexual Dysfunction, Cocaine-Induced Sleep Disorder and Cocaine-Related Disorder Not Otherwise Specified (292.9); Hallucinogen-Related Disorders such as Hallucinogen Dependence (304.50), Hallucinogen Abuse (305.30), Hallucinogen Intoxication (292.89), Hallucinogen Persisting Perception Disorder (Flashbacks) (292.89), Hallucinogen Intoxication Delirium, Hallucinogen-Induced Psychotic Disorder, Hallucinogen-Induced Mood Disorder, Hallucinogen-Induced Anxiety Disorder and Hallucinogen-Related Disorder Not Otherwise Specified (292.9); Inhalant-Related Disorders such as Inhalant Dependence (304.60), Inhalant Abuse (305.90), Inhalant Intoxication (292.89), Inhalant Intoxication Delirium, Inhalant-Induced Persisting Dementia, Inhalant-Induced Psychotic Disorder, Inhalant-Induced Mood Disorder, Inhalant-Induced Anxiety Disorder and Inhalant-Related Disorder Not Otherwise Specified (292.9); Nicotine-Related Disorders such as Nicotine Dependence (305.1), Nicotine Withdrawal (292.0) and Nicotine-Related Disorder Not Otherwise Specified (292.9); Opioid-Related Disorders such as Opioid Dependence (304.00), Opioid Abuse (305.50), Opioid Intoxication (292.89), Opioid Withdrawal (292.0), Opioid Intoxication Delirium, Opioid-Induced Psychotic Disorder, Opioid-Induced Mood Disorder, Opioid-Induced Sexual Dysfunction, Opioid-Induced Sleep Disorder and Opioid-Related Disorder Not Otherwise Specified (292.9); Phencyclidine (or Phencyclidine-Like)-Related Disorders such as Phencyclidine Dependence (304.60), Phencyclidine Abuse (305.90), Phencyclidine Intoxication (292.89), Phencyclidine Intoxication Delirium, Phencyclidine-Induced Psychotic Disorder, Phencyclidine-Induced Mood Disorder, Phencyclidine-Induced Anxiety Disorder and Phencyclidine-Related Disorder Not Otherwise Specified (292.9); Sedative-, Hypnotic-, or Anxiolytic-Related Disorders such as Sedative, Hypnotic, or Anxiolytic Dependence (304.10), Sedative, Hypnotic, or Anxiolytic Abuse (305.40), Sedative, Hypnotic, or Anxiolytic Intoxication (292.89), Sedative, Hypnotic, or Anxiolytic Withdrawal (292.0), Sedative, Hypnotic, or Anxiolytic Intoxication Delirium, Sedative, Hypnotic, or Anxiolytic Withdrawal Delirium, Sedative-, Hypnotic-, or Anxiolytic-Persisting Dementia, Sedative-, Hypnotic-, or Anxiolytic-Persisting Amnestic Disorder, Sedative-, Hypnotic-, or Anxiolytic-Induced Psychotic Disorder, Sedative-, Hypnotic-, or Anxiolytic-Induced Mood Disorder, Sedative-, Hypnotic-, or Anxiolytic-Induced Anxiety Disorder Sedative-, Hypnotic-, or Anxiolytic-Induced Sexual Dysfunction, Sedative-, Hypnotic-, or Anxiolytic-Induced Sleep Disorder and Sedative-, Hypnotic-, or Anxiolytic-Related Disorder Not Otherwise Specified (292.9); Polysubstance-Related Disorder such as Polysubstance Dependence (304.80); and Other (or Unknown) Substance-Related Disorders such as Anabolic Steroids, Nitrate Inhalants and Nitrous Oxide.

In addition the compounds of formula (I) or their pharmaceutically acceptable salts may be of use for the treatment or prophylaxis of feeding disorders such as bulimia nervosa, binge eating, obesity, including obesity observed in Type 2 (non-insulin-dependent) diabetes patients. Further, the compounds of formula (I) or their pharmaceutically acceptable salts may be of use for the treatment or prophylaxis of stroke, particularly ischemic or haemorrhagic stroke and/or in blocking an emetic response i.e. nausea and vomiting.

The numbers in brackets after the listed diseases refer to the classification code in DSM-IV: Diagnostic and Statistical Manual of Mental Disorders, 4th Edition, published by the American Psychiatric Association. The various subtypes of the disorders mentioned herein are contemplated as part of the present invention.

The invention also provides a method for the treatment of a disease or disorder in a subject, for example those diseases and disorders mentioned hereinabove, comprising administering to said subject an effective amount of a compound of formula (I), or a pharmaceutically acceptable salt thereof.

The invention also provides a compound of formula (I), or a pharmaceutically acceptable salt thereof, for use in the treatment or prophylaxis of a disease or disorder, for example those diseases and disorders mentioned hereinabove.

The invention also provides the use of a compound of formula (I), or a pharmaceutically acceptable salt thereof, in the manufacture of a medicament for use in the treatment or prophylaxis of a disease or disorder, for example those diseases and disorders mentioned hereinabove.

For use in therapy the compounds of the invention are usually administered as a pharmaceutical composition. The invention also provides a pharmaceutical composition comprising a compound of formula (I), or a pharmaceutically acceptable salt thereof, and a pharmaceutically acceptable carrier.

The compounds of formula (I) or their pharmaceutically acceptable salts may be administered by any convenient method, e.g. by oral, parenteral, buccal, sublingual, nasal, rectal or transdermal administration, and the pharmaceutical compositions adapted accordingly.

The compounds of formula (I) or their pharmaceutically acceptable salts which are active when given orally can be formulated as liquids or solids, e.g. as syrups, suspensions, emulsions, tablets, capsules or lozenges.

A liquid formulation will generally consist of a suspension or solution of the active ingredient in a suitable liquid carrier(s) e.g. an aqueous solvent such as water, ethanol or glycerine, or a non-aqueous solvent, such as polyethylene glycol or an oil. The formulation may also contain a suspending agent, preservative, flavouring and/or colouring agent.

A composition in the form of a tablet can be prepared using any suitable pharmaceutical carrier(s) routinely used for preparing solid formulations, such as magnesium stearate, starch, lactose, sucrose and cellulose.

A composition in the form of a capsule can be prepared using routine encapsulation procedures, e.g. pellets containing the active ingredient can be prepared using standard carriers and then filled into a hard gelatin capsule; alternatively a dispersion or suspension can be prepared using any suitable pharmaceutical carrier(s), e.g. aqueous gums, celluloses, silicates or oils and the dispersion or suspension then filled into a soft gelatin capsule.

Typical parenteral compositions consist of a solution or suspension of the active ingredient in a sterile aqueous carrier or parenterally acceptable oil, e.g. polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active ingredient in a pharmaceutically acceptable aqueous or non-aqueous solvent and are usually presented in single or multidose quantities in sterile form in a sealed container which can take the form of a cartridge or refill for use with an atomising device. Alternatively the sealed container may be a disposable dispensing device such as a single dose nasal inhaler or an aerosol dispenser fitted with a metering valve. Where the dosage form comprises an aerosol dispenser, it will contain a propellant which can be a compressed gas e.g. air, or an organic propellant such as a fluorochlorohydrocarbon or hydrofluorocarbon. Aerosol dosage forms can also take the form of pump-atomisers.

Compositions suitable for buccal or sublingual administration include tablets, lozenges and pastilles where the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches.

In one embodiment the composition is in unit dose form such as a tablet, capsule or ampoule.

The composition may contain from 0.1% to 100% by weight, for example from 10 to 60% by weight, of the active material, depending on the method of administration. The composition may contain from 0% to 99% by weight, for example 40% to 90% by weight, of the carrier, depending on the method of administration. The composition may contain from 0.05 mg to 1000 mg, for example from 1.0 mg to 500 mg, of the active material, depending on the method of administration. The composition may contain from 50 mg to 1000 mg, for example from 100 mg to 400 mg of the carrier, depending on the method of administration. The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 1.0 to 500 mg, and such unit doses may be administered more than once a day, for example two or three a day. Such therapy may extend for a number of weeks or months.

Orexin-A (Sakurai, T. et al (1998) Cell, 92 pp 573-585) can be employed in screening procedures for compounds which inhibit the ligand's activation of the orexin-1 or orexin-2 receptors.

In general, such screening procedures involve providing appropriate cells which express the orexin-1 or orexin-2 receptor on their surface. Such cells include cells from mammals, yeast, *Drosophila* or *E. coli*. In particular, a polynucleotide encoding the orexin-1 or orexin-2 receptor is used to transfect cells to express the receptor. The expressed receptor is then contacted with a test compound and an orexin-1 or orexin-2 receptor ligand, as appropriate, to observe inhibition of a functional response. One such screening procedure involves the use of melanophores which are transfected to express the orexin-1 or orexin-2 receptor, as described in WO 92/01810.

Another screening procedure involves introducing RNA encoding the orexin-1 or orexin-2 receptor into *Xenopus* oocytes to transiently express the receptor. The receptor oocytes are then contacted with a receptor ligand and a test compound, followed by detection of inhibition of a signal in the case of screening for compounds which are thought to inhibit activation of the receptor by the ligand.

Another method involves screening for compounds which inhibit activation of the receptor by determining inhibition of binding of a labelled orexin-1 or orexin-2 receptor ligand to cells which have the orexin-1 or orexin-2 receptor (as appropriate) on their surface. This method involves transfecting a eukaryotic cell with DNA encoding the orexin-1 or orexin-2 receptor such that the cell expresses the receptor on its surface and contacting the cell or cell membrane preparation with a compound in the presence of a labelled form of an orexin-1 or orexin-2 receptor ligand. The ligand may contain a radioactive label. The amount of labelled ligand bound to the receptors is measured, e.g. by measuring radioactivity.

Yet another screening technique involves the use of FLIPR equipment for high throughput screening of test compounds that inhibit mobilisation of intracellular calcium ions, or other ions, by affecting the interaction of an orexin-1 or orexin-2 receptor ligand with the orexin-1 or orexin-2 receptor as appropriate.

Throughout the specification and claims which follow, unless the context requires otherwise, the word 'comprise', and variations such as 'comprises' and 'comprising' will be understood to imply the inclusion of a stated integer or step or group of integers or steps but not to the exclusion of any other integer or step or group of integers or steps.

All publications, including but not limited to patents and patent applications, cited in this specification are herein incorporated by reference as if each individual publication were specifically and individually indicated to be incorporated by reference herein as though fully set forth.

The following Examples illustrate the preparation of certain compounds of formula (I) or salts thereof. The Descriptions 1 to 40 illustrate the preparation of intermediates used to make compounds of formula (I) or salts thereof.

In the procedures that follow, after each starting material, reference to a description is typically provided. This is provided merely for assistance to the skilled chemist. The starting material may not necessarily have been prepared from the Description referred to.

The yields were calculated assuming that products were 100% pure if not stated otherwise.

The compounds described in the Examples described hereinafter have all been prepared as a first step from stereochemically pure starting materials. The stereochemistry of the compounds of the Descriptions and Examples have been assigned on the assumption that the absolute configuration of these centres are retained. The relative stereochemistry of the compounds of the Descriptions and Examples have been assigned on the assumption that the relative stereochemistry is maintained as determined by using Rotating frame 2D ROESY experiments in the chiral intermediates phenylmethyl (1S,4S,6S)-4-({[(1,1-dimethylethyl)(diphenyl)silyl]oxy}methyl)-3-azabicyclo[4.1.0]heptane-3-carboxylate (D8) and 1,1-dimethylethyl (1S,4S,6S)-4-(hydroxymethyl)-3-azabicyclo[4.1.0]heptane-3-carboxylate (D27). In some Examples the relative stereochemistry has been confirmed on the final compounds as well.

Compounds are named using ACD/Name PRO6.02 chemical naming software (Advanced Chemistry Development Inc., Toronto, Ontario, M5H2L3, Canada).

Proton Magnetic Resonance (NMR) spectra were recorded either on Varian instruments at 400, 500 or 600 MHz, or on a Bruker instrument at 400 MHz. Chemical shifts are reported in ppm ($\delta$) using the residual solvent line as internal standard. Splitting patterns are designed as s, singlet; d, doublet; t, triplet; q, quartet; m, multiplet; b, broad. The NMR spectra were recorded at a temperature ranging from 25 to 90° C. When more than one conformer was detected the chemical shifts for the most abundant one is usually reported.

Unless otherwise specified, HPLC analyses indicated by HPLC (walk-up): rt (retention time)=x min, were performed on a Agilent 1100 series instrument using a Luna 3u C18(2) 100 A column (50×2.0 mm, 3 μm particle size) [Mobile phase and Gradient: 100% (water+0.05% TFA) to 95% (acetonitrile+0.05% TFA) in 8 min. Column T=40° C. Flow rate=1 mL/min UV detection wavelength=220 nm]. Other HPLC analyses, indicated by HPLC (walk-up, 3 min method), were performed using an Agilent Zorbax SB-C18 column (50×3.0 mm, 1.8 μm particle size) [Mobile phase and Gradient: 100% (water+0.05% TFA) to 95% (acetonitrile+0.05% TFA) in 2.5 min, hold 0.5 min Column T=60° C. Flow rate=1.5 mL/min UV detection wavelength=220 nm].

In the analytical characterization of the described compounds "MS" refers to Mass Spectra taken by Direct infusion Mass or to Mass Spectra associated with peaks taken by UPLC/MS or HPLC/MS analysis, where the Mass Spectrometer used is as mentioned below. Direct infusion Mass spectra (MS) were run on a Agilent MSD 1100 Mass Spectrometer, operating in ES (+) and ES (−) ionization mode [ES (+): Mass range: 100-1000 amu. Infusion solvent: water+0.1% $HCO_2H/CH_3CN$ 50/50. ES (−): Mass range: 100-1000 amu. Infusion solvent: water+0.05% $NH_4OH/CH_3CN$ 50/50]

UV and MS spectra associated with the peaks were taken on HPLC instrument Agilent 1100 Series coupled to an Agilent LC/MSD 1100 Mass Spectrometer operating in positive or negative electrospray ionization mode and in both acidic and basic gradient conditions

[Acidic gradient LC/MS–ES (+ or −): analyses performed on a Supelcosil ABZ+Plus column (33×4.6 mm, 3 μm). Mobile phase: A—water+0.1% $HCO_2H$/B—$CH_3CN$.

Gradient (standard method): t=0 min 0% (B), from 0% (B) to 95% (B) in 5 min lasting for 1.5 min, from 95% (B) to 0% (B) in 0.1 min, stop time 8.5 min Column temperature=room temperature. Flow rate=1 mL/min Gradient (fast method): t=0 min 0% (B), from 0% (B) to 95% (B) in 3 min lasting for 1 min, from 95% (B) to 0% (B) in 0.1 min, stop time 4.5 min Column T=room temperature. Flow rate=2 mL/min.

Basic gradient LC/MS–ES (+ or −): analyses performed on a XTerra MS C18 column (30×4.6 mm, 2.5 μm). Mobile phase: A—5 mM aq. $NH_4HCO_3$+ammonia (pH 10)/B—$CH_3CN$. Gradient: t=0 min 0% (B), from 0% (B) to 50% (B) in 0.4 min, from 50% (B) to 95% (B) in 3.6 min lasting for 1 min, from 95% (B) to 0% (B) in 0.1 min, stop time 5.8 min column temperature=room temperature. Flow rate=1.5 mL/min]

Mass range ES (+ or −): 100-1000 amu. UV detection range: 220-350 nm. The usage of this methodology is indicated by "LC-MS" in the analytic characterization of the described compounds.

Total ion current (TIC) and DAD UV chromatographic traces together with MS and UV spectra associated with the peaks were taken on a UPLC/MS Acquity™ system equipped with 2996 PDA detector and coupled to a Waters Micromass ZQ™ Mass Spectrometer operating in positive or negative electrospray ionisation mode [LC/MS–ES (+ or −): analyses performed using an Acquity™ UPLC BEH C18 column (50× 21 mm, 1.7 μm particle size), column temperature 40° C.]. Mobile phase: A—water+0.1% HCOOH/B—$CH_3CN$+ 0.075% HCOOH, Flow rate: 1.0 mL/min, Gradient: t=0 min 3% B, t=0.05 min 6% B, t=0.57 min 70% B, t=1.4 min 99% B, t=1.45 min 3% B)]. The usage of this methodology is indicated by "UHPLC" in the analytic characterization of the described compounds.

[LC/MS–ES (+ or −): analyses performed using an Acquity™ BEH C18 column (50×2.1 mm, 1.7 μm particle size) column temperature 40° C.]. Mobile phase: A—water+ 0.1% $HCO_2H$/B—$CH_3CN$+0.06% or 0.1% $HCO_2H$. Gradient: t=0 min 3% B, t=1.5 min 100% B, t=1.9 min 100% B, t=2 min 3% B stop time 2 min Column T=40° C. Flow rate=1.0 mL/min. Mass range: ES (+): 100-1000 amu or ES(+): 50-800 amu. ES (−): 100-800 amu. UV detection range: 210-350 nm. The usage of this methodology is indicated by "UPLC (Acid IPQC)" in the analytic characterization of the described compounds.

[LC/MS–ES (+ or −): analyses performed using an Acquity™ BEH C18 column (50×2.1 mm, 1.7 μm particle size) column temperature 40° C.]. Mobile phase: A—water+ 0.1% $HCO_2H$/B—$CH_3CN$+0.06% or 0.1% $HCO_2H$. Gradient: t=0 min 3% B, t=0.05 min 6% B, t=0.57 min 70% B, t=1.06 min 99% B lasting for 0.389 min, t=1.45 min 3% B, stop time 1.5 min Column temperature=40° C. Flow rate=1.0 mL/min Mass range: ES (+): 100-1000 amu or ES(+): 50-800 amu, ES (−): 100-800 amu. UV detection range: 210-350 nm The usage of this methodology is indicated by "UPLC (Acid QC_POS_50-800 or GEN_QC or FINAL_QC)" in the analytic characterization of the described compounds.

[LC/MS–ES (+ or −): analyses performed using an Acquity™ BEH C18 column (50×2.1 mm, 1.7 μm particle size) column temperature 40° C.]. Mobile phase: A—water+ 0.1% $HCO_2H$/B—$CH_3CN$+0.06% or 0.1% $HCO_2H$. Gradient: t=0 min 3% B, t=1.06 min 99% B, t=1.45 min 99% B, t=1.46 min 3% B, stop time 1.5 min Column temperature=40° C.

Flow rate=1.0 mL/min Mass range: ES (+): 100-1000 amu. ES (−): 100-800 amu. UV detection range: 210-350 nm. The usage of this methodology is indicated by "UPLC (Acid GEN_QC_SS)" in the analytic characterization of the described compounds.

Total ion current (TIC) and DAD UV chromatographic traces together with MS and UV spectra associated with the peaks were taken on a UPLC/MS Acquity™ equipped with PDA detector and coupled to a Waters SQD mass spectrometer operating in positive and negative alternate electrospray ionisation mode [LC/MS-ES(+ or −): analyses performed using an Acquity™ BEH C18 column (50×2.1 mm, 1.7 μm particle size) column temperature 40° C. Mobile phase: A—10 mM aqueous solution of $NH_4HCO_3$ (adjusted to pH 10 with ammonia)/B—$CH_3CN$. Gradient: t=0 min 3% B, t=1.06 min 99% B lasting for 0.39 min, t=1.46 min 3% B, stop time 1.5 min Column T=40° C. Flow rate=1.0 mL/min. Mass range: ES (+): 100-1000 amu or ES (+): 50-800 amu. ES (−): 100-1000 amu. UV detection range: 220-350 nm. The usage of this methodology is indicated by "UPLC (Basic GEN_QC or QC_POS_50-800)" in the analytic characterization of the described compounds.

Unless otherwise specified, Preparative LC-MS purifications were run on a MDAP (Mass Detector Auto Purification) Waters instrument (MDAP FractionLynx). [LC/MS–ES (+): analyses performed using a Gemini C18 AXIA column (50× 21 mm, 5 μm particle size). Mobile phase: A—$NH_4HCO_3$ sol. 10 mM, pH 10; B—$CH_3CN$. Flow rate: 17 mL/min. The gradient will be specified each time].

Preparative LC-MS purifications were also run on a MDAP (Mass Detector Auto Purification) Waters instrument. The usage of this methodology is indicated by "Fraction Lynx" in the analytic characterization of the described compounds.

For reactions involving microwave irradiation, a Personal Chemistry Emrys™ Optimizer was used.

In a number of preparations, purification was performed using Biotage manual flash chromatography (Flash+), Biotage automatic flash chromatography (Horizon, SP1 and SP4), Companion CombiFlash (ISCO) automatic flash chromatography, Flash Master Personal or Vac Master systems.

Flash chromatography was carried out on silica gel 230-400 mesh (supplied by Merck AG Darmstadt, Germany), Varian Mega Be—Si pre-packed cartridges, pre-packed Biotage silica cartridges (e.g. Biotage SNAP cartridge), KP-NH prepacked flash cartridges or ISCO RediSep Silica cartridges.

SPE-SCX cartridges are ion exchange solid phase extraction columns supplied by Varian. The eluent used with SPE-SCX cartridges is DCM and MeOH or only MeOH followed by 2 N ammonia solution in MeOH. The collected fractions are those eluted with the ammonia solution in MeOH.

SPE-Si cartridges are silica solid phase extraction columns supplied by Varian.

The following table lists the used abbreviations:

| | |
|---|---|
| ACN | Acetonitrile |
| AcOH | Acetic acid |
| BINAP | 2, 2'-bis(diphenylphosphino)-1, 1'-binaphtalene |
| bs or br.s | broad signal |
| Boc | t-Butoxycarbonyl |
| CV | Column Volume |
| Cy | Cyclohexanes |
| DCE | Dichloroethane |
| DCM | Dichloromethane |

| | |
|---|---|
| Dess-Martin | 1,1,1-Tris(acetoxy)-1,1-dihydro-1,2-benziodoxol-3-(1H)-one Periodinane |
| DIAD | Diisopropyl azodicarboxylate |
| DIBAL-H | Diisobutylaluminum hydride |
| DIPEA | N,N-Diisopropyl-N-ethylamine |
| DMF | Dimethylformamide |
| DMSO | Dimethylsulfoxide |
| EtOAc | Ethylacetate |
| EtOH | Ethanol |
| eq | equivalent |
| KHMDS | Hexamethyldisilazane potassium salt |
| MeOH | Methanol |
| MsCl | Mesyl chloride |
| Ph | Phenyl |
| pH = 5 buffer | Acetic acid/KOAc 1 M in water solution |
| rt | retention time |
| T | temperature |
| TBDPS | tert-Butyl diphenylsilyl |
| TBTU | O-(benzotriazol-1-yl)-N,N,N',N'-tetramethyluronium tetrafluoroborate |
| TEA | Triethylamine |
| TEMPO | 2,2,6,6-Tetramethylpiperidine-1-oxyl |
| TFA | Trifluoroacetic acid |
| THF | Tetrahydrofuran |

DESCRIPTIONS

Description 1: (3S)-4-Hydroxy-3-({[(phenylmethyl)oxy]carbonyl}amino)butanoic acid (D1)

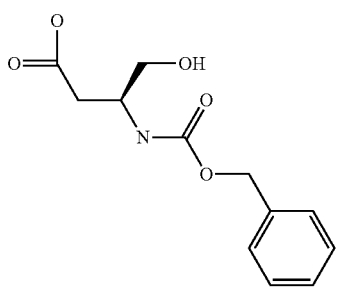

In a 500 ml round-bottomed flask phenylmethyl [(3S)-5-oxotetrahydro-3-furanyl]carbamate (4.3 g, 18.28 mmol, available from Sigma-Aldrich # 419249) was dissolved in water (100 ml) and acetone (100 ml) and to this solution $Cs_2CO_3$ (10.72 g, 32.9 mmol) was added and the reaction left under stirring at room temperature for 5 hours. The solution was then transferred into a separatory funnel and washed with EtOAc (2×50 ml). The aqueous phase was then acidified to pH=2 by the addition of a 2 M HCl aqueous solution and then extracted with EtOAc (5×100 mls). The organic phase was dried ($Na_2SO_4$) and solvent removed under reduced pressure to give the title compound D1 (3.78 g) as a white solid. MS: (ES/+) m/z: 254 (M+1). $C_{12}H_{15}NO_5$ requires 253. $^1$H NMR (400 MHz, DMSO-$d_6$) δ (ppm): 12.11 (bs, 1 H), 7.41-7.07 (m, 5 H), 5.17-4.92 (m, 2 H), 3.95-3.62 (m, 1 H), 3.42-3.22 (m, 2H), 2.55-2.40 (m, 1 H), 2.34-2.23 (m, 1 H).

Description 2: (3S)-4-{[(1,1-Dimethylethyl)(diphenyl)silyl]oxy}-3-({[(phenylmethyl)oxy]carbonyl}amino)butanoic acid (D2)

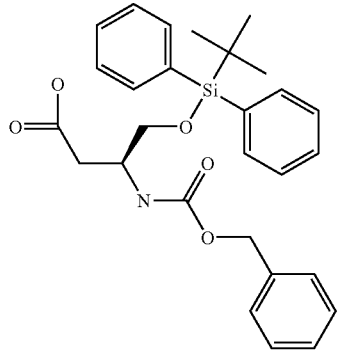

In a 250 ml round-bottomed flask (3S)-4-hydroxy-3-({[(phenylmethyl)oxy]carbonyl}amino)butanoic acid D1 (3.75 g), was dissolved in DMF (30 ml). To the resulting solution imidazole (3.02 g, 44.4 mmol), and TBDPSCl (7.61 ml, 29.6 mmol) were added and the resulting solution left under stirring at room temperature for 15 hours. The reaction mixture was transferred into separatory funnel containing water (300 ml). The pH of the medium was lowered to pH=2 by the addition of a 2 M HCl aqueous solution, then extracted with EtOAc (5×50 mls). The collected organic phase was dried ($Na_2SO_4$) and volatiles removed under reduced pressure to give a slightly yellow oil. This crude oil was transferred into a 250 ml round bottom flask with THF (50 ml) and MeOH (10 ml) was added. To the resulting mixture a $K_2CO_3$ aqueous solution (9 g of $K_2CO_3$ dissolved in 10 ml of water) was added and the reaction left under stirring at room temperature for 3 hours. Volatiles were removed under vacuum and the thick oil obtained was diluted in water (200 ml) and EtOAc (200 ml) and charged into a separatory funnel. The phases were separated and to the organic one water (200 ml) was added and the pH of the medium adjusted to pH=2 by the addition of a 2 M HCl aqueous solution. The phases were separated and the aqueous one back extracted with EtOAc (5×50 mls). The collected organic phases were dried ($Na_2SO_4$) and solvent removed under reduced pressure to give an oil that was purified by flash chromatography on silica gel (DCM/MeOH from 100/0 to 90/10). Collected fractions gave the title compound D2 (5.2 g) as a colorless oil. MS: (ES/+) m/z: 492 (M+1). $C_{28}H_{33}NO_5Si$ requires 491. $^1$H NMR (400 MHz, DMSO-$d_6$) δ ppm 8.05-8.28 (m, 4 H), 7.72-8.00 (m, 11 H), 5.47-5.59 (m, 2 H), 4.64-4.80 (m, 1 H), 4.17-4.34 (m, 2 H), 3.20-3.31 (m, 1 H), 3.06-3.20 (m, 1 H), 1.41-1.58 (m, 9 H).

Description 3: Methyl (3S)-4-{[(1,1-dimethylethyl)(diphenyl)silyl]oxy}-3-({[(phenylmethyl)oxy]carbonyl}amino)butanoate (D3)

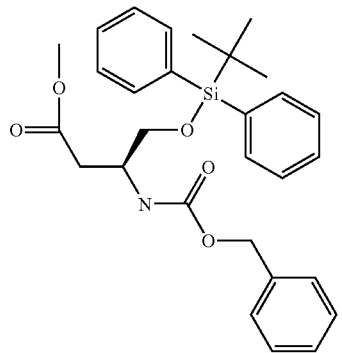

In a 1000 ml round-bottomed flask (3S)-4-{[(1,1-dimethylethyl)(diphenyl)silyl]oxy}-3-({[(phenylmethyl)oxy]carbonyl}amino)butanoic acid D2 (15 g) was dissolved in DMF (200 ml). To this solution DIPEA (28.8 ml, 165 mmol) and TBTU (11.46 g, 35.7 mmol) were added and the solution left under stirring at room temperature for 20 minutes. After this time to the brown solution MeOH (11 ml) was added and the mixture left under stirring at room temperature for 30 minutes. The reaction mixture was transferred into a separatory funnel containing brine (600 ml) and extracted with EtOAc (5×200 ml). The organic phases were washed with water (3×100 ml), dried (Na$_2$SO$_4$) and evaporated under vacuum to give an orange oil. This material was purified by column chromatography on silica gel (flash master, Cy/EtOAc from 100/0 to 80/20) to give the title compound D3 (13.9 g) as a yellow solid. MS: (ES/+) m/z: 506 (M+1). C$_{29}$H$_{35}$NO$_5$Si requires 505. $^1$H NMR (400 MHz, CDCl$_3$-d$_6$) δ (ppm): 7.69-7.29 (m, 15 H), 5.4-5.26 (m, 1 H), 5.11 (m, 2 H), 4.25-4.14 (m, 1 H), 3.82-3.68 (m, 2H), 3.64 (s, 3 H), 2.79-2.52 (m, 2 H), 1.08 (s, 9 H).

Description 4: Phenylmethyl [(1S)-1-({[(1,1-dimethylethyl)(diphenyl)silyl]oxy}methyl)-3-oxopropyl]carbamate (D4a, D4b, D4c)

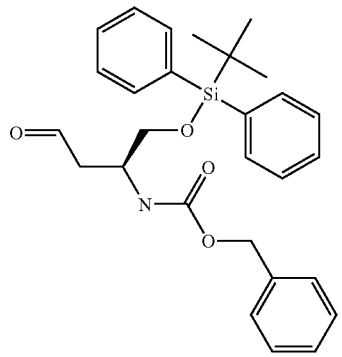

In a 500 ml round-bottomed flask methyl (3S)-4-{[(1,1-dimethylethyl)(diphenyl)silyl]oxy}-3-({[(phenylmethyl)oxy]carbonyl}amino)butanoate D3 (6.28 g) was dissolved in DCM (79 ml) and cooled to −78° C. To the solution DIBAL-H 1 M solution in THF (62.1 ml, 62.1 mmol) was added dropwise and the reaction mixture left under stirring at −78° C. for 1 hour. After this time a NH$_4$Cl saturated aqueous solution was added (200 ml) and the mixture left to warm to room temperature. The resulting mixture was filtered through a celite pad and the gelly solid was washed with DCM (5×100 ml). The combined organic phases were dried (Na$_2$SO$_4$) and evaporated under reduced pressure to give a yellow oil, which was purified by column chromatography on silica gel (SP4, SNAP 340 g, Cy/EtOAc from 100/0 to 50/50) and two products were recovered:

A) the title compound D4a (3.7 g) as white solid. HPLC (walk-up): rt=7.59 min. MS: (ES/+) m/z: 476 (M+1). C$_{28}$H$_{33}$NO$_4$Si requires 475. $^1$H NMR (400 MHz, CDCl$_3$-d$_6$) δ (ppm): 9.73 (s, 1 H), 7.74-7.30 (m, 15 H), 5.24-5.0 (m, 3 H), 4.36-4.11 (m, 1 H), 3.91-3.65 (m, 2 H), 2.88-2.61 (m, 2 H), 1.08 (s, 9 H); and B) phenylmethyl [(1S)-1-({[(1,1-dimethylethyl)(diphenyl)silyl]oxy}methyl)-3-hydroxypropyl]carbamate (1 g) as colorless oil. HPLC (walk-up): rt=7.33 min. MS: (ES/+) m/z: 478 (M+1). C$_{28}$H$_{35}$NO$_4$Si requires 477. $^1$H NMR (400 MHz, CDCl$_3$-d$_6$) δ (ppm): 7.74-7.30 (m, 15 H), 5.24-4.99 (m, 3 H), 4.0-3.52 (m, 5 H), 3.21-2.96 (m, 1 H), 1.64-1.91 (m, 2H), 1.08 (s, 9 H).

In a 250 ml round-bottomed flask phenylmethyl [(1S)-1-(1-({[(1,1-dimethylethyl)(diphenyl)silyl]oxy}methyl)-3-hydroxypropyl]carbamate (1 g, 2.094 mmol), was dissolved in DCM (50 ml). To the solution NaHCO$_3$ (0.528 g, 6.28 mmol) and Dess-Martin periodinane (0.977 g, 2.303 mmol) were added and the resulting mixture left under stirring at room temperature for 4.5 hours. The reaction mixture was transferred into a separatory funnel containing a saturated NaHCO$_3$ aqueous solution (150 mls) and extracted with DCM (4×40 mls), dried (Na$_2$SO$_4$) and the solvent removed under reduced pressure to give a pale yellow oil. This material was purified by column chromatography on silica gel (SP4 SNAP 50 g, Cy/EtOAc from 1/0 to 8/2). Collected fractions gave the title compound D4b (0.970 g) as a colorless oil. D4a (3.7 g) and D4b (0.970 g) were joined together to give the title compound D4c (4.67 g). HPLC (walk-up): rt=7.59 min MS: (ES/+) m/z: 476 (M+1). C$_{28}$H$_{33}$NO$_4$Si requires 475. $^1$H NMR (400 MHz, CDCl$_3$-d$_6$) δ (ppm): 9.73 (s, 1 H), 7.74-7.30 (m, 15 H), 5.24-5.0 (m, 3 H), 4.36-4.11 (m, 1 H), 3.91-3.65 (m, 2 H), 2.88-2.61 (m, 2 H), 1.08 (s, 9 H).

Description 5: Methyl (2Z,5S)-6-{[(1,1-dimethylethyl)(diphenyl)silyl]oxy}-5-({[(phenylmethyl)oxy]carbonyl}amino)-2-hexenoate (D5)

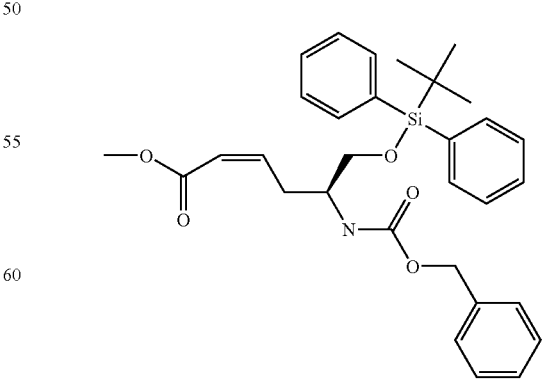

In a 500 ml round-bottomed flask methyl {bis[(2,2,2-trifluoroethyl)oxy]phosphoryl}acetate (2.077 ml, 9.82 mmol)

and 18-Crown-6-ether (12.98 g, 49.1 mmol) were dissolved in THF (100 ml) and cooled at −78° C. To this solution KHMDS 0.5 M in toluene (19.64 ml, 9.82 mmol) was slowly added. After 30 minutes at this temperature, phenylmethyl [(1S)-1-(1-({[(1,1-dimethylethyl)(diphenyl)silyl]oxy}methyl)-3-oxopropyl]carbamate D4c (4.67 g) dissolved in THF (50 ml) was added dropwise and the reaction left under stirring at −78° C. for 30 minutes. A saturated NH$_4$Cl aqueous solution was added (300 ml) and the mixture transferred into a separatory funnel and extracted with EtOAc (3×80 mls). The organic phase was dried (Na$_2$SO$_4$) and evaporated to give a yellowish oil. This material was purified by column chromatography on silica gel (SP4 SNAP 340 g, Cy/EtOAc from 100/0 to 80/20). Collected fractions gave the title compound D5 (3.58 g) as colorless oil. HPLC (walk-up): rt=8.04 min MS: (ES/+) m/z: 532 (M+1). C$_{31}$H$_{37}$NO$_5$Si requires 531. $^1$H NMR (400 MHz, CDCl$_3$-d$_6$) δ (ppm): 7.74-7.30 (m, 15 H), 6.32-6.20 (m, 1 H), 5.90-5.75 (m, 1 H), 5.25-5.18 (m, 1 H), 5.08 (m, 2 H), 4.0-3.83 (m, 1 H), 3.76-3.56 (m, 5 H), 3.18-2.76 (m, 2 H), 1.07 (s, 9 H).

Description 6: Phenylmethyl [(1S,3Z)-1-({[(1,1-dimethylethyl)(diphenyl)silyl]oxy}methyl)-5-hydroxy-3-penten-1-yl]carbamate (D6)

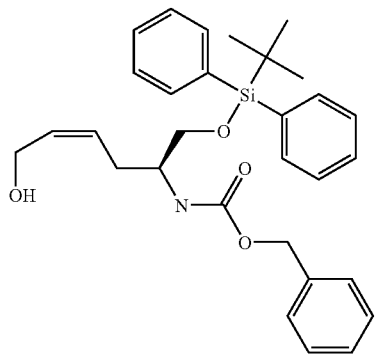

In a 500 ml round-bottomed flask methyl (2Z,5S)-6-{[(1,1-dimethylethyl)(diphenyl)silyl]oxy}-5-({[(phenylmethyl)oxy]carbonyl}amino)-2-hexenoate D5 (3.58 g) was dissolved in dry DCM (122 ml) and the solution cooled at −78° C. To this solution DIBAL-H 1 M in THF (33.7 ml, 33.7 mmol) was added dropwise and the mixture left under stirring at −78° C. for 5 hours. After this time a saturated NH$_4$Cl aqueous solution (250 ml) was added and the reaction mixture filtered through a celite pad the solid was washed with DCM (5×200 ml) and the resulting filtrate transferred into a separatory funnel. The phases were separated and the aqueous one back extracted with DCM (3×100 mls). The collected organic phases were dried (Na$_2$SO$_4$) and solvent removed under reduced pressure to give an oil. This crude was purified by column chromatography on silica gel (SP4 SNAP 340 g, Cy/EtOAc from 100/0 to 80/20). Collected fractions gave the title compound D6 (3.3 g) as colorless thick oil. HPLC (walk-up): rt=7.30 min. C$_{30}$H$_{37}$NO$_4$Si requires 503. $^1$H NMR (400 MHz, CDCl$_3$-d$_6$) δ (ppm): 7.74-7.30 (m, 15 H), 5.71 (m, 1 H), 5.52 (m, 1 H), 5.80-5.61 (m, 1 H), 561-3.36 (m, 1 H), 5.20-4.94 (m, 2 H), 4.25-3.98 (m, 2 H), 3.91-372 (m, 1 H), 3.72-3.58 (m, 2 H), 2.50-2.26 (m, 2 H), 1.07 (s, 9 H)

Description 7: Phenylmethyl ((1S)-2-{[(1,1-dimethylethyl)(diphenyl)silyl]oxy}-1-{[2-(hydroxymethyl)cyclopropyl]methyl}ethyl)carbamate (D7)

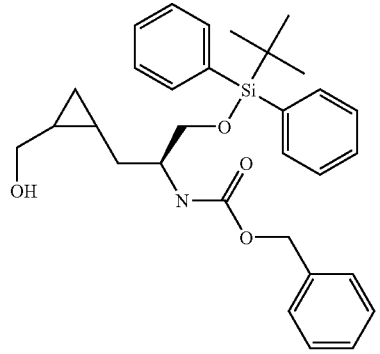

In a 25 ml round-bottomed flask diethylzinc 1M in hexane (65.5 ml, 65.5 mmol) and DCM (82 ml) were added and the resulting solution cooled at 0° C. To this solution TFA (5.05 ml, 65.5 mmol) was added dropwise and the mixture left under stirring at 0° C. for 20 minutes. After this time diiodomethane (5.29 ml, 65.5 mmol) was added dropwise to the solution and left under stirring for additional 20 minutes. In a 5 ml round-bottomed flask phenylmethyl [(1S,3Z)-1-({[(1,1-dimethylethyl)(diphenyl)silyl]oxy}methyl)-5-hydroxy-3-penten-1-yl]carbamate D6 (3.3 g) was dissolved DCM (82 ml) and the resulting solution added dropwise at 0° C. to the previously prepared solution of diethylzinc/TFA/CH$_2$I$_2$ in DCM. The resulting solution was left under stirring at room temperature for 30 minutes, then it was quenched with a saturated NH$_4$Cl aqueous solution (300 ml). The suspension was transferred into a separatory funnel and extracted with DCM (4×30 mls). The organic phases were dried (Na$_2$SO$_4$) and evaporated under reduced pressure to give an oil. This material was purified by column chromatography on silica gel (SP4 SNAP 340 g, Cy/EtOAc from 100/0 to 50/50). Two products were obtained:

A) single diastereoisomer 1 D7 (1.37 g) HPLC (walk-up): rt=7.52 min MS: (ES/+) m/z: 518 (M+1). C$_{31}$H$_{39}$NO$_4$Si requires 517. $^1$NMR: (400 MHz, CDCl$_3$-d$_6$) δ (ppm): 7.29-7.71 (m, 15 H), 5.54-5.63 (d, 1 H), 5.03-5.21 (m, 2 H), 4.01-3.86 (m, 1 H), 3.86-3.66 (m, 3 H), 3.43-3.26 (t, 1 H), 2.80-2.70 (br.s, 1 H), 1.96-1.81 (m, 1 H), 1.50-1.37 (m, 1 H), 1.17-1.09 (m, 1H), 1.08 (s, 9 H), 0.74-0.59 (m, 2 H), −0.07 (m, 1 H); and B) single diastereoisomer 2 (1.26 g). HPLC (walk-up): rt=7.38 min MS: (ES/+) m/z: 518 (M+1). C$_{31}$H$_{39}$NO$_4$Si requires 517.

Description 8: Phenylmethyl (1S,4S,6S)-4-({[(1,1-dimethylethyl)(diphenyl)silyl]oxy}methyl)-3-azabicyclo[4.1.0]heptane-3-carboxylate (D8)

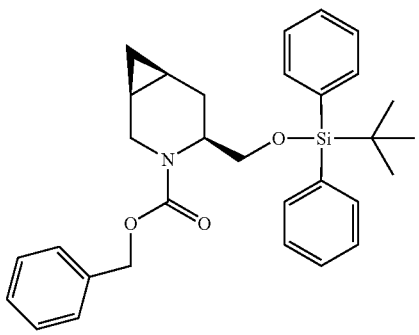

To an ice cooled solution of phenylmethyl ((1S)-2-{[(1,1 dimethylethyl)(diphenyl)silyl]oxy}-1-{[2-(hydroxymethyl)cyclopropyl]methyl}ethyl)carbamate single diastereoisomer 1 D7 (1.18 g) in DCM (35 ml) and TEA (0.953 ml, 6.84 mmol) was added mesyl chloride (0.355 ml, 4.56 mmol) and the resulting mixture was stirred for 3 hours. After this time the solvent was removed under reduced pressure and the white solid obtained was dissolved in DMF (47 ml), the solution was cooled to 0° C. and NaH (0.730 g, 18.25 mmol, 8 eq) was added and ice bath was removed. After stirring overnight more NaH (0.365 g, 9.12 mmol, 4 eq) was added to the ice cooled mixture and stirred at room temperature for 3 hours. UPLC showed starting material and desired product in 1:1 ratio, so NaH (0.180 g, 4.5 mmol, 1.97 eq) was added at room temperature and stirred for 2.5 hours. A saturated solution of NH$_4$Cl (300 ml) was added and extracted with EtOAc (3×50 mls), the organic phase was separated, dried (Na$_2$SO$_4$), filtered and evaporated to give a yellow oil which was purified via Biotage SP4 (silica gel, SNAP 100 g column; eluted with a gradient of Cy/EtOAc from 1/0 to 9/1). Collected fractions gave the title compound D8 (0.930 g) as a colourless oil. MS: (ES/+) m/z: 500 (M+1). C$_{31}$H$_{37}$NO$_3$Si requires 499. $^1$H NMR (400 MHz, DMSO-d$_6$) δ (ppm): 7.76-7.31 (m, 15 H), 5.16-4.84 (m, 2 H), 4.37 (br.s, 1 H), 3.83-3.68 (m, 1 H), 3.68-3.52 (m, 2 H), 2.37-2.22 (m, 2 H), 1.39-1.18 (m, 1 H), 1.13-1.01 (m, 1 H), 0.95 (s, 9 H), 0.92-0.83 (m, 1 H), 0.79-0.70 (m, 1 H), 0.33-0.04 (m, 1 H).

Description 9: Phenylmethyl (1S,4S,6S)-4-(hydroxymethyl)-3-azabicyclo[4.1.0]heptane-3-carboxylate (D9)

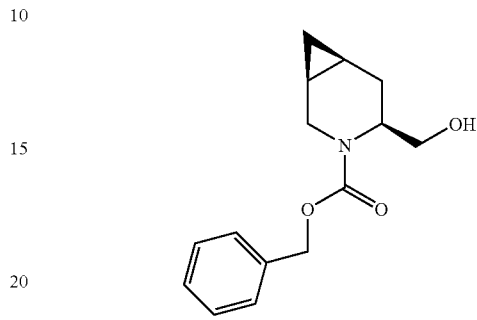

To an ice cooled solution of phenylmethyl (1S,4S,6S)-4-({[(1,1-dimethylethyl)(diphenyl)silyl]oxy}methyl)-3-azabicyclo[4.1.0]heptane-3-carboxylate D8 (0.930 g) in pyridine (14 ml) was added HF-pyridine (2.642 ml, 30.4 mmol), the resulting mixture was stirred for 20 minutes at 0° C. and then was slowly warmed to room temperature and stirred for 30 minutes. Water (200 ml) and EtOAc (30 ml) were added and stirred for 15 minutes. The organic phase was separated and the aqueous phase was extracted with EtOAc (6×5 mls). The collected organic layers were dried (Na$_2$SO$_4$), filtered and evaporated under reduced pressure to obtain an oil which was purified via Companion CombiFlash (Silica gel, SNAP 100 g column; eluted with 20 CV of DCM/MeOH 98/2). Collected and evaporated fractions gave the title compound D9 (0.447 g). MS: (ES/+) m/z: 262 (M+1). C$_{15}$H$_{19}$NO$_3$ requires 261. $^1$H NMR (400 MHz, DMSO-d$_6$) δ (ppm): 7.51-7.24 (m, 5 H), 5.20-5.0 (m, 2 H), 4.73-4.48 (m, 1 H), 4.43-4.17 (m, 1 H), 3.71-3.51 (m, 1 H), 3.51-2.35 (m, 2 H), 2.46-2.24 (m, 2 H), 1.20-0.95 (m, 2 H), 0.95-0.59 (m, 2 H), 0.21-0.09 (m, 1 H).

Description 10: Phenylmethyl (1S,4S,6S)-4-formyl-3-azabicyclo[4.1.0]heptane-3-carboxylate (D10)

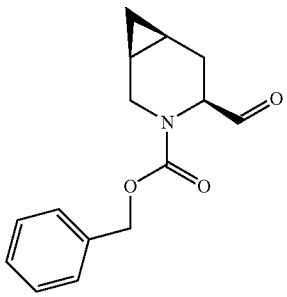

To a solution of phenylmethyl (1S,4S,6S)-4-(hydroxymethyl)-3-azabicyclo[4.1.0]heptane-3-carboxylate D9 (0.447 g) in DCM (13 ml) was added NaHCO$_3$ (0.575 g, 6.84 mmol) and Dess-Martin periodinane (0.798 g, 1.882 mmol) and stirred at room temperature. TLC (Cyclohexane/EtOAc 1/1, 2,4-dinitrophenylidrazine) showed the absence of starting material, so a solution of saturated NaHCO$_3$/5% Na$_2$S$_2$O$_3$ (60 ml) and DCM (10 ml) were added to the reaction mixture and it was left stirring for 30 minutes. The aqueous phase was back extracted with DCM (3×10 mls) and the biphasic system was passed through a phase separator cartridge. The organic solvent was evaporated under reduced pressure to yield a yellowish oil purified via Biotage SP4 (silica gel, SNAP 25 g; Cy/EtOAc, 25 CV from 1/0 to 7/3). Collected fractions gave the title compound D10 (0.370 g). MS: (ES/+) m/z: 260 (M+1), $C_{15}H_{17}NO_3$ requires 259. $^1$H NMR (400 MHz, DMSO-$d_6$) δ (ppm): 9.50-9.38 (m, 1 H), 7.48-7.18 (m, 5 H), 5.19-4.93 (m, 2 H), 4.31-3.83 (m, 2 H), 3.28-2.90 (m, 1 H), 2.30-2.15 (m, 1H), 1.77-1.30 (m, 1 H), 1.21-0.84 (m, 2 H), 0.56-0.75 (m, 1 H), 0.22-0.03 (m, 1 H).

Description 11: Phenylmethyl (1S,4S,6S)-4-({[5-(trifluoromethyl)-2-pyridinyl]amino}methyl)-3-azabicyclo[4.1.0]heptane-3-carboxylate (D11)

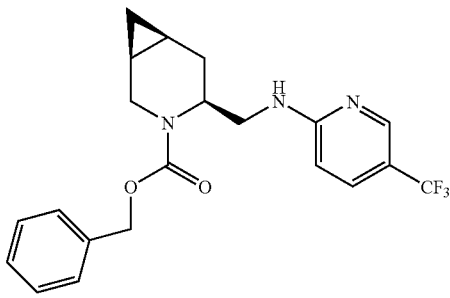

To a solution of phenylmethyl (1S,4S,6S)-4-formyl-3-azabicyclo[4.1.0]heptane-3-carboxylate D10 (0.370 g) in DCM (3.5 ml) were added AcOH (0.408 ml, 7.13 mmol) and 5-(trifluoromethyl)-2-pyridinamine (0.393 g, 2.4 mmol, 1.3 eq).

After 1 hour stirring, conversion into imine was not complete and so further 5-(trifluoromethyl)-2-pyridinamine (0.231 g, 1.425 mmol, 1 eq) was added and stirred for additional 3.5 hours. The reaction was cooled to 0° C. and sodium triacetoxyborohydride (2.419 g, 11.41 mmol) was added to give a thick suspension, the ice bath was removed, DCM (22.5 ml) was added and the resulting suspension was stirred overnight. A aqueous saturated solution of $Na_2CO_3$ (50 ml) and DCM (20 ml) were added to the reaction mixture which was vigorously stirred for 15 minutes. The organic phase was separated and the aqueous was back extracted with DCM (2×5 mls). Collected organic layers were dried through a phase separator cartridge and evaporated under reduced pressure to give pale yellow oil which was purified via Combi-Flash Companion (silica gel, SNAP 50 g column; Cy/EtOAc, 8/2). Collected fractions gave as colourless oil the title compound D11 (0.275 g). HPLC (walk-up): rt=5.11 minutes. MS: (ES/+) m/z: 406 (M+1). $C_{21}H_{22}F_3N_3O_2$ requires 405. $^1$H NMR (500 MHz, DMSO-$d_6$) δ (ppm): 8.25-8.0 (m, 1 H), 7.65-7.44 (m, 1 H), 7.44-7.18 (m, 6 H), 6.73-6.35 (m, 1 H), 5.18-4.99 (m, 1 H), 4.40-4.08 (m, 1 H), 3.96-3.72 (m, 1 H), 3.54-3.36 (m, 2H), 2.48-2.37 (m, 1 H), 2.29-2.15 (m, 1 H), 1.16-0.94 (m, 2 H), 0.0.89-0.76 (m, 1 H), 0.74-0.59 (m, 1 H), 0.27-0.09 (m, 1 H).

Description 12: N-[(1S,4S,6S)-3-Azabicyclo[4.1.0]hept-4-ylmethyl]-5-(trifluoromethyl)-2-pyridinamine (D12)

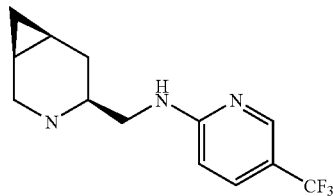

In a 250 ml hydrogenation flask phenylmethyl (1S,4S,6S)-4-({[5-(trifluoromethyl)-2-pyridinyl]amino}methyl)-3-azabicyclo[4.1.0]heptane-3-carboxylate D11 (0.275 g) was dissolved in MeOH (20 ml) and Pd/C (0.0722 g, 0.068 mmol) was added. The resulting suspension was hydrogenated at atmospheric pressure. After 25 min UPLC (Acid GEN_QC) showed a main side product with rt=0.99, peak observed: 284 (M+1). The Pd/C was filtered on a celite pad, the solvent was removed under reduced pressure to give an off-white semi-solid. This solid was dissolved in anhydrous EtOAc (20 ml) and Pd/C (0.0722 g, 0.068 mmol) was added. The suspension was hydrogenated at atmospheric pressure for 50 minutes (total time). The Pd/C was filtered on a celite pad, the solvent was removed under reduced pressure to give a yellowish solid, which was purified via Biotage SP4 (NH 25+M column; Cy/EtOAc: 1/0 to 75/25 15 CV, 75/25 3 CV, to 0/1 20 CV) to give the title compound D12 (0.100 g). HPLC (walk-up): rt=3.19 min MS: (ES/+) m/z: 272 (M+1). $C_{13}H_{16}F_3N_3$ requires 271. $^1$H NMR (400 MHz, DMSO-$d_6$) δ ppm 8.22-8.32 (m, 1 H), 7.57-7.64 (m, 1 H), 7.21-7.28 (m, 1 H), 6.60 (d, 1 H), 3.12-3.26 (m, 1 H), 2.89-3.10 (m, 3 H), 2.37-2.47 (m, 1 H), 1.83-1.94 (m, 1 H), 1.05-1.18 (m, 1 H), 0.69-0.98 (m, 2 H), 0.42-0.52 (m, 1 H), 0.28-0.39 (m, 1 H).

Description 13: [3-(Ethyloxy)-6-methyl-2-pyridinyl]methanol (D13)

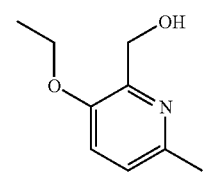

2-(hydroxymethyl)-6-methyl-3-pyridinol (1.5 g, 10.78 mmol, available from Sigma-Aldrich #144428), $K_2CO_3$ (7.45 g, 53.9 mmol) and iodoethane (1.724 ml, 21.56 mmol) were dissolved in DMF (15 ml). The mixture was left stirring at room temperature overnight. Water and EtOAc were added and the two layers were separated. The aqueous one was back-extracted several times with EtOAc. The combined organic phases were washed with brine/ice, dried ($Na_2SO_4$), filtered and concentrated under reduced pressure to afford the crude title compound D13 (1.67 g) as a pale yellow solid which was used in the next step without any further purification. MS: (ES/+) m/z: 168 (M+1). $C_9H_{13}NO_2$ requires 167. $^1$H-NMR (400 MHz, CDCl$_3$) δ (ppm): 6.96-7.07 (m, 2 H), 4.71 (s, 2 H), 4.04 (q, 2 H), 2.50 (s, 3 H), 1.43 (t, 3 H).

Description 14: [6-Methyl-3-(propyloxy)-2-pyridinyl]methanol was prepared using a similar procedure to that described above for Description 13. The compound of description 14 was obtained by O-alkylation of 2-(hydroxymethyl)-6-methyl-3-pyridinol and a suitable electrophile. This is provided merely for assistance to the skilled chemist. The starting material may not necessarily have been prepared from the batch referred to.

| No. | Structure | Characterising data |
|---|---|---|
| D14 | 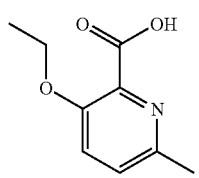 | [6-methyl-3-(propyloxy)-2-pyridinyl]methanol<br>MS: (ES/+) m/z: 182 (M + 1). $C_{10}H_{15}NO_2$ requires 181. $^1$H-NMR (400 MHz, $CDCl_3$) δ ppm: 7.03 (m, 2H), 4.73 (s, 2H), 4.50 (bs, 1H), 3.94 (t, 2H), 2.51 (s, 3H), 1.83 (m, 2H), 1.05 (t, 3H). |

Description 15:
3-(Ethyloxy)-6-methyl-2-pyridinecarboxylic acid (D15)

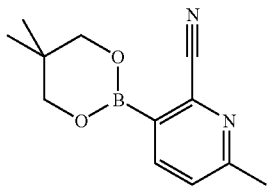

To a solution of [3-(ethyloxy)-6-methyl-2-pyridinyl]methanol D13 (1.67 g, material obtained in the Description 13) in acetonitrile (50 ml) and phosphate buffer (38 ml), TEMPO (0.22 g, 1.40 mmol) was added and the mixture was heated to 35° C. $NaClO_2$ (4.51 g, 49.90 mmol) in water (10 ml) and NaClO (13 wt % aqueous solution, 18.96 ml, 39.90 mmol) were added simultaneously over 1 hour. The resulting reaction mixture was stirred at 35° C. for 4 hours, water (40 ml) was added and the pH was adjusted to pH=8 by addition of a 1 M aqueous NaOH solution. The mixture was poured into an ice-cooled aqueous saturated sodium thiosulfate solution (100 ml) and stirred for a further 30 minutes. The pH was adjusted to pH=3 by addition of a 1 M aqueous HCl solution and the aqueous phase was extracted with DCM. The combined organic layers were washed with brine, dried ($Na_2SO_4$) and concentrated under reduced pressure to afford the title compound D15 (1.64 g). MS: (ES/+) m/z: 182 (M+1). $C_9H_{11}NO_3$ requires 181. $^1$H-NMR (400 MHz, DMSO-$d_6$) δ (ppm): 12.50-13.26 (bs., 1 H), 7.49 (d, 1 H), 7.31 (d, 1 H), 4.08 (q, 2 H), 2.40 (s, 3 H), 1.29 (t, 3 H).

Description 16:
6-Methyl-3-(propyloxy)-2-pyridinecarboxylic acid (D16)

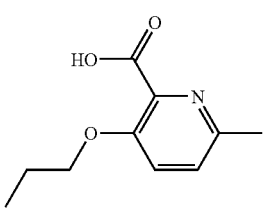

In a 500 ml round-bottom flask [6-methyl-3-(propyloxy)-2-pyridinyl]methanol D14 (3.50 g) was suspended in water (16 ml) and $KMnO_4$ (6.10 g, 38.60 mmol) and KOH (1 M aqueous solution, 19 ml, 19 mmol) were added. The mixture was stirred at room temperature for 2 hours. The pH was adjusted to pH=4 by addition of a 1 M aqueous HCl solution and then MeOH (100 ml) was added. The solid was filtered off, volatiles were removed under reduced pressure and the aqueous phase was extracted twice with DCM. The collected organic layers were washed with brine, dried ($Na_2SO_4$) and concentrated under reduced pressure to afford the title compound D16 (2 g). MS: (ES/+) m/z: 196 (M+1). $C_{10}H_{13}NO_2$ requires 195. $^1$H-NMR (400 MHz, DMSO-$d_6$) δ (ppm): 12.96 (bs, 1 H), 7.49 (d, 1 H), 7.31 (d, 1 H), 3.98 (t, 2H), 2.40 (s, 3 H), 1.60-1.80 (m, 2 H), 0.96 (t, 3 H).

Description 17: 3-(5,5-Dimethyl-1,3,2-dioxaborinan-2-yl)-6-methyl-2-pyridinecarbonitrile (D17)

2,2,6,6-tetramethylpiperidine (3.49 ml, 20.52 mmol) was dissolved in dry THF (25 ml) under argon and stirred at −30° C.; BuLi (13.33 ml, 21.33 mmol) 1.6 M in hexane was added over 5 min (the temperature never exceeded −25° C.). The yellow solution was stirred at −30° C. for 20 min, then chilled at −78° C. and tris(1-methylethyl) borate (4.38 ml, 18.96 mmol) was added over 5 min (the temperature never exceeded −73° C.).

After 10 min at −78° C., 6-methyl-2-pyridinecarbonitrile (2.0 g, 16.93 mmol) dissolved in dry THF (14 ml) was added dropwise (over 20 min) maintaining internal temperature below −73° C. and the mixture became dark-brown. The mixture was stirred at −73° C. for 2 hours. The mixture was quenched with AcOH (2.374 ml, 41.5 mmol) dropwise at −73° C. (the temperature never exceeded −60° C. and the mixture became brilliant orange). The cooling bath was removed and the mixture left to reach the room temperature: during this period the mixture became thick and new THF (8 ml) had to be added in order to have a better stirring. The mixture was stirred 10 min at room temperature then 2,2-dimethyl-1,3-propanediol (2.409 g, 23.13 mmol) was added in one portion and the mixture stirred at room temperature overnight.

The solvent was evaporated and the orange residue taken-up with DCM (100 ml) and 10% water solution of $KH_2PO_4$ (100 ml). The phases were separated and the water phase was back-extracted with DCM (50 ml). The combined organic phases were washed with 10% water solution of $KH_2PO_4$ (50 ml). The DCM was evaporated. The residue was dissolved in $Et_2O$ (100 ml) and extracted with NaOH 0.05 M (5×50 ml, boronic ester in water phase). The aqueous phases were joined together and the pH was adjusted between pH=4 and pH=5 with 10% water solution of KH$_2$PO$_4$ (50 ml). The so obtained yellow solution was extracted with AcOEt (3×200 mls). All the organics joined together were dried (Na$_2$SO$_4$) and evaporated the title compound D17 (2.29 g) of as yellow oil, that solidified on standing. C$_{12}$H$_{15}$BN$_2$O$_2$ requires 230. $^1$H NMR (400 MHz, CDCl$_3$) δ ppm 7.97-8.15 (m, 1 H), 7.31-7.36 (m, 1 H), 3.85 (m, 4 H), 2.52-2.73 (s, 3 H), 0.97-1.10 (m, 6 H).

Description 18:
6-Methyl-3-(2-pyrimidinyl)-2-pyridinecarbonitrile (D18)

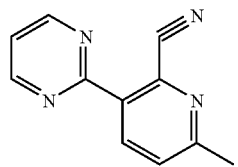

A) Isopropylmagnesium chloride-LiCl (37.9 ml, 36.5 mmol) was added portion wise (in overall 10 min) to a solution of 3-bromo-6-methyl-2-pyridinecarbonitrile (4 g, 20.30 mmol) in THF (150 ml) cooled to −70° C. (internal temperature). The reaction was kept to that temperature for 15 min. Then it was allowed to gently warm up to −40° C. in overall 1 hour. Then, it was cooled to −78° C. and zinc chloride (3.32 g, 24.36 mmol) was added. The resulting mixture was allowed to warm up to room temperature in 1 hour. Pd(Ph$_3$P)$_4$ (2.346 g, 2.030 mmol), 2-chloropyrimidine (3 g, 26.2 mmol) were added and the mixture was refluxed (external temperature 100° C.) until complete consumption of starting chloropyrimidine (3 hours). The reaction mixture was cooled to room temperature and poured into water (200 ml) cooled to 10° C. It was then extracted with EtOAc (5×200 mls). The collected organic phases, containing large amount of colloid material and water, were washed with brine (200 ml). The water phase was filtered over a gouch, and the solid material was washed with further EtOAc 2×300 mls). The collected organic phases were dried overnight over Na$_2$SO$_4$, filtered and concentrated to give (7 g) the crude material which was purified (Biotage Sp1 over a 240 g Silica Anolgix column, with a 25 g pre-column) to give the title compound D18 as yellow solid (1.8 g). UPLC (Acid GEN_QC_SS): rt=0.58 minutes, peak observed: 197 (M+1). C$_{11}$H$_8$N$_4$ requires 196.

B) An alternative route to make D18 is: 3-(5,5-dimethyl-1,3,2-dioxaborinan-2-yl)-6-methyl-2-pyridinecarbonitrile D17 (50.6 mg) was dissolved 1,4-Dioxane (1 ml) under nitrogen in a vial, then 2-bromopyrimidine (42.0 mg, 0.264 mmol), CsF (67 mg, 0.441 mmol), Pd(Ph$_3$P)$_4$ (12 mg, 10.38 μmol) and CuI (7 mg, 0.037 mmol) were added in sequence. The vial was then capped and stirred at 65° C., after 1 hour the solvent was removed at reduced pressure and the residue partitioned between AcOEt (10 mls) and NaHCO$_3$ (saturated solution, 10 ml). The phases were separated and the water was extracted with AcOEt (2×10 mls). The organic fraction were joined together, dried over Na$_2$SO$_4$ and evaporated at reduced pressure, obtaining an orange oily residue which was purified (Biotage, Snap 25 g silica gel column, AcOEt/Cy from pure Cy to 50:50 in 10 column volumes) to obtain the title compound D18 as pale yellow solid (27.6 mg).

Description 19:
6-Methyl-3-(2-pyrimidinyl)-2-pyridinecarboxylic acid (D19)

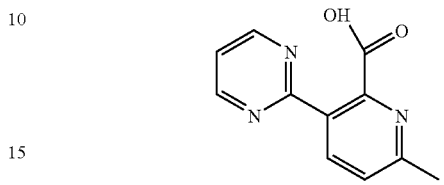

A) 6-methyl-3-(2-pyrimidinyl)-2-pyridinecarbonitrile D18 (0.8 g) was reacted in 6 M aqueous HCl (40 ml, 240 mmol) at 80° C. for 3 hours, then solvent was removed under vacuum, and the resulting crude was purified (70 g Varian C18 column conditioning with MeOH (120 mls), then water (120 mls), loading in water, washing with water (200 mls), product eluted with 100% MeOH) to give the title compound D19 (0.6 g) as yellow solid. UPLC (Acid GEN_QC_SS): rt=0.30 minutes, peak observed: 216 (M+1). C$_{11}$H$_9$N$_3$O$_2$ requires 217. $^1$H NMR (400 MHz, DMSO-d$_6$) δ ppm 13.07 (bs, 1 H), 8.78-9.01 (m, 2 H), 8.39 (m, 1 H), 7.39-7.67 (m, 2 H), 2.56-2.67 (s, 3 H).

B) An alternative method to make D19 is as follows: 6-methyl-3-(2-pyrimidinyl)-2-pyridinecarbonitrile D18 (0.481 g) was suspended in EtOH (5 ml) and a solution of NaOH (0.490 g, 12.26 mmol) in water (5 ml) was added. The yellow mixture was stirred at 100° C. overnight. The yellow solution was cooled to 25° C. and HCl 6 M (1.0 ml) was added dropwise till pH=4.5. The solvent was removed to give a yellow powder that was dried at 50° C./vacuum for 1.5 hours to give the title compound D19 (1.242 g).

Description 20: (2S)-2-amino-4-penten-1-ol (D20)

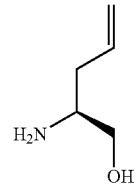

In a 20 L reactor, to a suspension of (2S)-2-amino-4-pentenoic acid (available from Sigma-Aldrich #285013) (200 g, 1319 mmol) in THF dry (3200 ml) stirred under nitrogen at 0° C. was added a solution of LiAlH$_4$ (1600 ml, 1600 mmol) 1 M in THF dropwise in 1.5 hours (maintaining internal temperature between 0° C. and 5° C.). The reaction mixture was stirred at 25° C. for 2 hours (white suspension). The check by TLC (DCM/MeOH 1/1, AcOH 0.5% ninhidrine) showed reaction to be completed. The reaction mixture was cooled to 0° C. and was quenched by adding in sequence: 60.7 ml of water (1 ml H$_2$O×1 g of LiAlH$_4$)+60.7 ml of NaOH 1 N (1 ml NaOH 1M×1 g of LiAlH$_4$)+182 ml of water (3 ml H$_2$O×1 g of LiAlH$_4$). The suspension was stirred at room temperature for 1 hour then the precipitate was filtered over sodium sulphate (gooch n3) and washed with Et$_2$O (6 L) and DCM (4 L). The solvent was evaporated (temperature bath 30° C.) of the crude title compound D20 (110 g) as pale-orange oil. MS: (ES/+) m/z: 102 (M+1). C$_5$H$_{11}$NO requires 101. $^1$H-NMR (400

MHz, DMSO-$d_6$) δ ppm 1.39 (br. s, 2 H) 1.81-1.96 (m, 1 H) 2.06-2.19 (m, 1 H) 2.59-2.73 (m, 1H) 3.14 (dd, 1 H) 3.26 (dd, 1 H) 4.48 (br. s, 1 H) 4.91-5.09 (m, 2 H) 5.71-5.92 (m, 1 H)

Description 21: 1,1-dimethylethyl (2-{[(1S)-1-(hydroxymethyl)-3-buten-1-yl]amino}-2-oxoethyl)carbamate (non-preferred name) (D21)

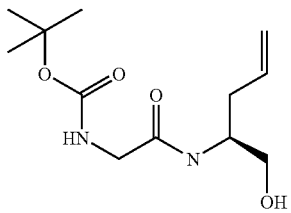

In a 5 L reactor, to a solution of (2S)-2-amino-4-penten-1-ol D20 (110 g of the crude title compound prepared in the description D20) in THF (660 ml) and MeOH (440 ml) stirred at 0° C. (+5° C. internal) was added triethylamine (182 ml, 1305 mmol) and 2,5-dioxo-1-pyrrolidinyl N-{[(1,1-dimethylethyl)oxy]carbonyl}glycinate (available from Sigma-Aldrich #15423) (237 g, 870 mmol) portionwise over 15 min. The reaction mixture was stirred at 2° C. (internal temperature) for 3 hours. TLC check (TLC-$NH_2$, DCM/MeOH 95/5, potassium permanganate) showed residual starting material. Further 2,5-dioxo-1-pyrrolidinyl N-{[(1,1-dimethylethyl)oxy]carbonyl}glycinate (60 g, 220 mmol) was added and the mixture stirred at 2° C. for 1 hour. TLC check (TLC-$NH_2$, DCM/MeOH 95/5, potassium permanganate) showed residual starting material. Further 2,5-dioxo-1-pyrrolidinyl N-{[(1,1-dimethylethyl)oxy]carbonyl}glycinate (40 g, 146 mmol) was added and the mixture stirred at 2° C. for 1 hours. TLC check (TLC-$NH_2$, DCM/MeOH 95/5, potassium permanganate) showed residual starting material but the work-up was carried out. The reaction mixture was poured into aqueous saturated solution of $NH_4Cl$ (3400 ml) and AcOEt (1375 ml), then the phases were separated and the aqueous layer was back-extracted with AcOEt (1375 ml). The combined organic layers were washed with $NaHCO_3$ aqueous saturated solution (1031 ml) dried ($Na_2SO_4$) and evaporated to give crude material (268 g, deep brown). This residue was triturated with $Et_2O$ (687 ml) for 1 hour at 25° C. The solid was filtered (gooch n3), washed with $Et_2O$ (200 ml) and dried under vacuum to give the title compound D21 (87 g) as pale brown solid. Mother liquors (deep brown) were evaporated and the residue chromatographed (Biotage 75 L, silica column, eluting with DCM/MeOH 98/2, 95/5) to give (34 g) of residual brown product that was triturated with $Et_2O$ (200 ml). The solid was filtered, washed with $Et_2O$ and dried under vacuum to give a further batch of the title compound D21 (26 g) as pale brown solid. MS: (ES/+) m/z: 259 (M+1). $C_{12}H_{22}N_2O_4$ requires 258. $^1$H NMR (400 MHz, CDCl$_3$) δ ppm 1.47 (s, 9 H) 2.22-2.43 (m, 2 H) 2.68-2.83 (m, 1 H) 3.50-3.86 (m, 4 H) 3.94-4.09 (m, 1 H) 5.00-5.25 (m, 3 H) 5.64-5.89 (m, 1 H) 6.17-6.44 (m, 1 H)

Description 22: 1,1-dimethylethyl {2-[(4S)-2,2-dimethyl-4-(2-propen-1-yl)-1,3-oxazolidin-3-yl]-2-oxoethyl}carbamate (non-preferred name) (D22)

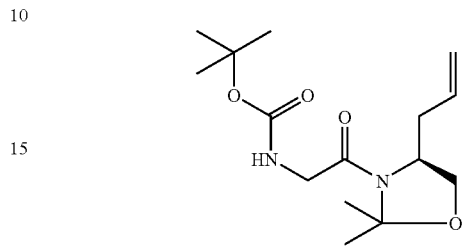

To a suspension of 1,1-dimethylethyl (2-{[(1S)-1-(hydroxymethyl)-3-buten-1-yl]amino}-2-oxoethyl)carbamate D21 (37 g) in toluene (370 ml) stirred at 25° C. were added 2,2-bis(methyloxy)propane (370 ml, 3020 mmol) and p-toluenesulfonic acid monohydrate (3.7 g, 19.45 mmol). The reaction mixture was stirred at reflux (85° C. internal, oil bath 105° C.) for 1.5 hour (clear solution). The check by TLC (DCM/MeOH 95/5) showed the reaction to be completed. The solvent was evaporated to obtain a brown oil that was chromatographed (Biotage 75 L, silica, eluting with Cy/EtOAc 8/2, 7/3) to give the title compound D22 (30 g) as yellow oil. UPLC (Acid GEN_QC): rt=0.69 minutes, peak observed: 299 (M+1). $C_{15}H_{26}N_2O_4$ requires 298. $^1$H NMR (400 MHz, CDCl$_3$) δ ppm 1.46 (s, 9 H) 1.54 (s, 3 H) 1.67 (s, 3 H) 2.30-2.49 (m, 2 H) 3.71-4.05 (m, 5 H) 5.04-5.22 (m, 2 H) 5.37-5.52 (m, 1 H) 5.65-5.81 (m, 1 H)

Description 23: trifluoromethanesulfonic acid-{2-[(4S)-2,2-dimethyl-4-(2-propen-1-yl)-1,3-oxazolidin-3-yl]-2-oxoethyl}amine (1:1) (D23)

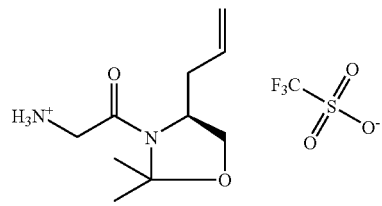

To a solution of 1,1-dimethylethyl {2-[(4S)-2,2-dimethyl-4-(2-propen-1-yl)-1,3-oxazolidin-3-yl]-2-oxoethyl}carbamate D22 (28.67 g) in DCM (300 ml) 2,6-dimethylpyridine (27.9 ml, 240 mmol) was added followed by trimethylsilyl trifluoromethanesulfonate (34.7 ml, 192 mmol) the mixture was stirred at room temperature for 30 min. The reaction was quenched with 2 ml of water and the solvent was removed under reduced pressure, the residue was charged on a Biotage 75 L column eluting with [DCM/MeOH 100:0 then 98:2 then 96:4 then 85:15]. Evaporation of the solvent gave: the title compound D23 (21 g). UPLC (Acid FINAL_QC): rt=0.36 minutes, peak observed: 199 (M+1−CHF$_3$O$_3$S)$C_{10}H_{18}N_2O_2$.CHF$_3$O$_3$S requires 348. $^1$H NMR (400 MHz, DMSO-$d_6$) δ ppm 1.40 (s, 3 H), 1.50 (s, 3 H), 2.17-2.43 1.40 (m, 2 H), 3.68-3.98 (m, 4 H), 3.99-4.09 (m, 1 H), 4.83-5.40 (m, 2 H), 5.58-5.97 (m, 1H), 7.63-8.36 (br.s., 2 H)

Description 24: (4S)-3-(diazoacetyl)-2,2-dimethyl-4-(2-propen-1-yl)-1,3-oxazolidine (D24)

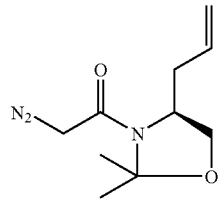

{2-[(4S)-2,2-dimethyl-4-(2-propen-1-yl)-1,3-oxazolidin-3-yl]-2-oxoethyl}amine trifluoromethansulfonate D23 (67.0 g) was dissolved in DCM (670 ml) and pH=5 Buffer solution (670 ml) and cooled to 2° C. (internal). Sodium nitrite (26.5 g, 385 mmol) dissolved in water (134 ml) was added dropwise to the reaction mixture stirred at 2° C. over 30 min. The reaction mixture was stirred at 3° C. for 2.5 hours. Phases were separated. Water phase was back-extracted with DCM (1×670 ml, 1×335 ml). The combined organic layers, dried ($Na_2SO_4$), were evaporated (bath temperature 30° C.) to give 43 g of crude product. This crude was purified over silica pad [(230-400 Mesh) eluting with Cy/EtOAc 8/2, 7/3, 6/4] to give the title compound D24 (36.58 g) as pale yellow oil. UPLC (Acid GEN_QC): rt=0.59 minutes, peak observed: 210 (M+1) $C_{10}H_{15}N_3O_2$ requires 209. $^1$H NMR (400 MHz, $CDCl_3$) δ ppm 1.58 (s, 3 H) 1.69 (s, 3 H) 2.25-2.50 (m, 2 H) 3.43-3.70 (m, 1 H) 3.82-4.01 (m, 2 H) 4.84 (s, 1 H) 5.09-5.24 (m, 2 H) 5.63-5.84 (m, 1 H)

Description 25: (5aS,6aS,7aS)-3,3-dimethylhexahydro-5 H-cyclopropa[d][1,3]oxazolo[3,4-a]pyridin-5-one and (5aR,6aR,7aS)-3,3-dimethylhexahydro-5H-cyclopropa[d][1,3]oxazolo[3,4-a]pyridin-5-one (D25A syn/D25B anti)

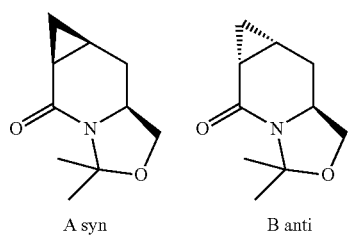

A syn    B anti (4S)-3-(diazoacetyl)-2,2-dimethyl-4-(2-propen-1-yl)-1,3-oxazolidine D24 (36.5 g) dissolved in DCM (365 ml) was added dropwise at 25° C. to a suspension of rhodium(II) acetate dimer (3.85 g, 8.72 mmol) in DCM (183 ml) over 2.5 hours. The resulting mixture was stirred at 25° C. for 30 minutes. From TLC (Cy/EtOAc 1/1): no more starting material. The mixture was filtered (gooch n 3), concentrated and chromatographed twice (over silica 230-400 Mesh, eluting with Cy/EtOAc 7/3, 6/4) to give three fractions that after trituration with n-heptane (40 ml, for each fraction) gave the following three batches:

D25B/D25A 95:3 (10.3 g, anti as major isomer anti/syn 95/3) HPLC (walk up): rt1=3.09 rt2=3.14 minutes;

D25A/D25B 31:68 (4.47 g, anti/syn roughly 31/68) HPLC (walk up): rt1=3.05 rt2=3.11 minutes;

D25A/D25B (10.5 g, D 25A syn as major isomer). HPLC (walk up): rt1=3.08 rt2=3.16 minutes. $^1$H NMR (500 MHz, $CDCl_3$) δ ppm 3.87-4.02 (m, 2 H), 3.32 (t, 1 H), 2.29-2.38 (m, 1 H), 1.57 (s, 3 H), 1.45-1.51 (m, 1 H), 1.43 (s, 3 H), 1.36-1.42 (m, 1 H), 1.12-1.20 (m, 1 H), 1.06-1.12 (m, 0 H), 0.45-0.54 (m, 1 H)

662 mg of this third batch of D25A/D25B were taken and purified by flash chromatography (Snap-50 g silica gel column, EtOAc/Cy from 100% Cy to 30:70). From this purification it was obtained a batch of almost pure cis isomer (the title compound D25A) (298 mg) as white solid, and a 347 g batch of a mixture of cis/trans isomers (75/25) as a colourless oil. UPLC (Basic GEN_QC): rt=0.48 minutes, peak observed: 182 (M+1). $C_{10}H_{15}NO_2$ requires 181. $^1$H NMR (400 MHz, $CDCl_3$) δ ppm 3.98-4.10 (m, 2 H) 3.36-3.45 (m, 1 H) 2.37-2.47 (m, 1 H) 1.66 (s, 3 H) 1.53-1.61 (m, 1 H) 1.52 (s, 3 H) 1.42-1.50 (m, 1 H) 1.14-1.29 (m, 2 H) 0.59 (m, 1 H)

Description 26: (1S,4S,6S)-4-(hydroxymethyl)-3-azabicyclo[4.1.0]heptan-2-one (D26)

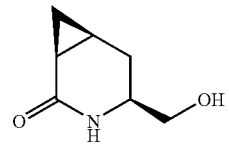

(5aS,6aS,7aS)-3,3-dimethylhexahydro-5H-cyclopropa[d][1,3]oxazolo[3,4-a]pyridin-5-one D25 (3.56 g) was dissolved in HCl (25 ml, 150 mmol) (6 M in water) into a 250 ml-round bottomed flask and the mixture was stirred at 40° C.: after 4 hours the reaction was complete. The solvent was evaporated at reduced pressure using a rotavapor (bath temperature: 40° C.). The oily residue was stripped with toluene and the residue dried under high vacuum for 3 hours, obtaining the title compound D26 as white solid (2.843 g). UPLC (Acid IPQC): rt=0.31 minutes, peak observed: 142 (M+1). $C_7H_{11}NO_2$ requires 141. $^1$H NMR (500 MHz, DMSO-$d_6$) d ppm 0.56-0.68 (m, 1 H) 0.93-1.05 (m, 1 H) 1.30-1.39 (m, 1 H) 1.39-1.48 (m, 1 H) 1.57-1.67 (m, 1 H) 1.98-2.09 (m, 1 H) 3.17-3.29 (m, 2 H) 3.31-3.40 (m, 1 H) 6.89-7.13 (m, 1 H)

Description 27: 1,1-dimethylethyl (1S,4S,6S)-4-(hydroxymethyl)-3-azabicyclo[4.1.0]heptane-3-carboxylate (D27)

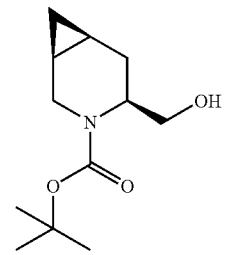

(1S,4S,6S)-4-(hydroxymethyl)-3-azabicyclo[4.1.0]heptan-2-one D26 (3.839 g) was suspended in THF (40 ml) then $BH_3$.THF (1 M THF solution, 136 ml, 136 mmol) was added slowly (over 5 minutes) and the resulting mixture stirred at reflux for 2 hours. The mixture was cooled to room temperature and then to 0° C. using an ice/water bath. MeOH (25 ml) was slowly added and, when the gas evolution stopped, HCl (3 M water solution, 140 ml, 420 mmol) was slowly added and the resulting mixture was stirred again at 85° C. for 1 hour. The mixture was cooled again to room temperature.

A second reaction mixture was prepared: (1S,4S,6S)-4-(hydroxymethyl)-3-azabicyclo[4.1.0]heptan-2-one D26 (100 mg) was suspended in THF (0.5 mL), then BH$_3$.THF (3.6 mL, 3.60 mmol) was added slowly (over 1 minute) and the resulting mixture stirred at reflux for 2 hours. This second mixture was chilled to room temperature, then HCl (3.6 mL, 10.80 mmol) was slowly added and the resulting mixture was stirred again at 75° C. for 1 hour. This mixture was chilled again to room temperature and then it was added to the first mixture to form a single mixture.

NaOH (3 M water solution, 140 ml, 420 mmol) was slowly added to the acidic mixture, then additional NaOH (50 ml, 150 mmol) was added in order to get a pH value of about 10. Boc$_2$O (7.13 ml, 30.7 mmol) was added dissolved in THF (30 ml) and the resulting biphasic mixture was stirred vigorously at room temperature overnight. New Boc$_2$O (4.57 ml, 19.70 mmol) was added dissolved in THF (20 ml) and the mixture stirred vigorously at room temperature for 1.5 hours. EtOAc (100 ml) was added to the mixture and the phases were separated. The water phase was extracted with EtOAc (3×100 mls) and all the organic fractions were mixed together. The so obtained organic solution was washed with brine (3×150 mls), dried over Na$_2$SO$_4$ and evaporated at reduced pressure, obtaining the crude target material as pale yellow oil (14 g). This material was purified by Biotage (Snap-340 g silica gel column, from pure Cy to EtOAc/Cy 70:30). It was obtained the title compound D27 (5.695 g) as colourless oil. MS: (ES/+) m/z: 228 (M+1) 128 (M+1−Boc). C$_{12}$H$_{21}$NO$_3$ requires 227. $^1$H NMR (500 MHz, DMSO-d$_6$) δ ppm 4.43 (t, 1 H), 4.00-4.20 (m, 1 H), 3.34-3.45 (m, 1 H), 3.25-3.31 (m, 2H), 2.10-2.23 (m, 1 H), 2.00-2.10 (m, 1 H), 1.30 (s, 9 H), 0.86-0.99 (m, 2 H), 0.66-0.77 (m, 1 H), 0.51-0.61 (m, 1 H), −0.04-0.05 (m, 1 H)

Description 28: 1,1-dimethylethyl (1S,4S,6S)-4-[(1, 3-dioxo-1,3-dihydro-2H-isoindol-2-yl)methyl]-3-azabicyclo[4.1.0]heptane-3-carboxylate (D28)

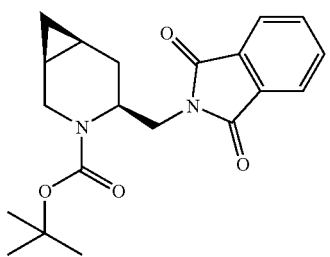

1,1-dimethylethyl (1S,4S,6S)-4-(hydroxymethyl)-3-azabicyclo[4.1.0]heptane-3-carboxylate D27 (310 mg), triphenylphosphine (1073 mg, 4.09 mmol) and phthalimide (502 mg, 3.41 mmol) were collected together and dissolved in THF (7 ml). The mixture was brought to 50° C. and then DIAD (0.796 ml, 4.09 mmol) was added dropwise. The mixture was stirred for 1 hour at 50° C. then 1 ml of water were added. Volatiles were removed in vacuum and the resulting crude was purified by silica gel chromatography (column size 10 g) using Cy/EtOAc=8:2 to Cy/EtOAc=5:5 to EtOAc 100%. It was recovered the title compound D28 (488 mg).

UPLC: (Acid Final_QC): rt=0.80 minutes, peaks observed: 357 (M+1). C$_{20}$H$_{24}$N$_2$O$_4$ requires 356.

Description 29: 1,1-dimethylethyl (1S,4S,6S)-4-(aminomethyl)-3-azabicyclo[4.1.0]heptane-3-carboxylate (D29)

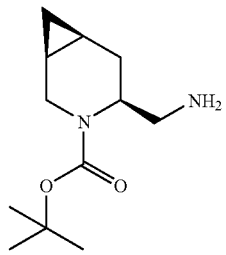

1,1-dimethylethyl (1S,4S,6S)-4-[(1,3-dioxo-1,3-dihydro-2H-isoindol-2-yl)methyl]-3-azabicyclo[4.1.0]heptane-3-carboxylate D28 (1.8 g) was dissolved in EtOH (8 ml) then hydrazine (2.476 ml, 50.5 mmol) was carefully added and the reaction stirred at room temperature for 2 hours. All volatiles were removed under vacuum and the solid residue was purified by SCX chromatography (column size 20 g using MeOH 100% to MeOH/NH3 2M). The product recovered showed a low purity so it was purified again by silica —NH chromatography (Biotage SP—column size 28 g using EtOAc 100% as eluent). It was recovered the title compound D29 (793 mg). UPLC: (Acid Final_QC): rt=0.46 minutes, peaks observed: 227 (M+1). C$_{12}$H$_{22}$N$_2$O$_2$ requires 226. $^1$H NMR (400 MHz, CDCl$_3$) δ ppm 4.41 (br. s., 1 H) 3.66 (br. s., 1 H) 2.90-2.65 (m, 2 H) 2.42-2.17 (m, 2 H) 1.60-1.40 (m, 11 H) 1.21-1.08 (m, 1 H) 1.06-0.84 (m, 2 H) 0.81-0.68 (m, 1 H) 0.30-0.04 (m, 1 H).

Description 30: 1,1-dimethylethyl (1S,4S,6S)-4-({[5-(trifluoromethyl)-2-pyrazinyl]amino}methyl)-3-azabicyclo[4.1.0]heptane-3-carboxylate (D30)

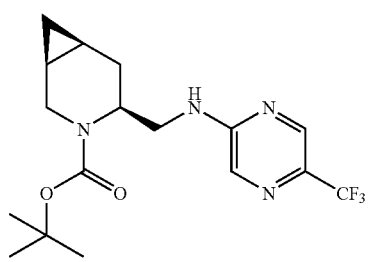

A) 1,1-dimethylethyl (1S,4S,6S)-4-(aminomethyl)-3-azabicyclo[4.1.0]heptane-3-carboxylate D29 (197 mg), 2-bromo-5-(trifluoromethyl)pyrazine (395 mg, 1.741 mmol), sodium tert-butoxide (125 mg, 1.306 mmol) tetrabutylammonium bromide (337 mg, 1.045 mmol), palladium(II) acetate (19.54 mg, 0.087 mmol) and BINAP (54.2 mg, 0.087 mmol) were collected together and dissolved in 1,4-dioxane (8 ml). The reaction was then stirred at 100° C. in a MW system (20 minutes×2). After cooling it was filtered through a Celite Pad, diluted with 20 ml of EtOAc and washed with 20 ml of Brine. The organic phase was dried over Na$_2$SO$_4$ anhydrous, filtered and concentrated under vacuum to give a crude product which was purified by silica chromatography (column size 25 g, using Cy:EtOAc=8:2 to 2:8). It was recovered the title compound D30 (100 mg). UPLC: (Acid Final_QC): rt=0.87 minutes, peaks observed: 373 (M+1). $C_{17}H_{23}F_3N_4O_2$ requires 372. $^1$H NMR (400 MHz, CDCl$_3$) δ ppm 8.25 (s, 1 H) 7.89 (s, 1 H) 4.37-4.02 (m, 2 H) 3.48-3.30 (m, 2 H) 2.53-2.20 (m, 2 H) 2.07 (s, 9 H) 1.30-1.15 (m, 1 H) 1.05-0.72 (m, 3 H) 0.30-0.03 (m, 1 H).

B) 1,1-dimethylethyl (1S,4S,6S)-4-(aminomethyl)-3-azabicyclo[4.1.0]heptane-3-carboxylate D29 (400 mg) and 2-bromo-5-(trifluoromethyl)pyrazine (401 mg, 1.767 mmol) were dissolved in DMF (2 ml) then sodium carbonate (375 mg, 3.53 mmol) was added and the mixture was heated to 50° C. for 2 hours. DMF was concentrated under vacuum and the residue was taken up with DCM (3 ml) and washed with NaHCO$_3$ saturated solution (4 ml). The organic phase was filtered through a phase separator tube, concentrated under vacuum and purified by silica gel chromatography (Biotage SP—column size 25 g SNAP using Cy:EtOAc=8:2 to 2:8 as eluent). It was recovered the title compound D30 (300 mg).

Description 31: N-[(1S,4S,6S)-3-azabicyclo[4.1.0]hept-4-ylmethyl]-5-(trifluoromethyl)-2-pyrazinamine (D31)

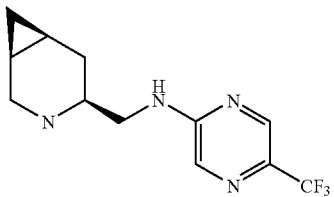

To a solution of 1,1-dimethylethyl (1S,4S,6S)-4-({[5-(trifluoromethyl)-2-pyrazinyl]amino}methyl)-3-azabicyclo[4.1.0]heptane-3-carboxylate D30 (100 mg) in DCM (4 ml) TFA (2 ml, 26.0 mmol) was added dropwise. The mixture was left reacting at room temperature for 2 hours. Solvent was evaporated in vacuum and the crude was purified by SCX chromatography using MeOH 100% to MeOH/NH3 2M. It was recovered the title compound D31 (57 mg). UPLC: (Acid Final_QC): rt=0.48 minutes, peaks observed: 273 (M+1). $C_{12}H_{15}F_3N_4$ requires 272. $^1$H NMR (400 MHz, CDCl$_3$). δ ppm 0.22-0.29 (m, 1 H) 0.67-0.76 (m, 1 H) 0.82-0.92 (m, 1 H) 1.02-1.13 (m, 1 H) 1.24-1.35 (m, 1 H) 2.01-2.12 (m, 1 H) 2.63-2.72 (m, 1 H) 2.95-3.06 (m, 1 H) 3.17 (dd, 1 H) 3.26 (d, 1 H) 3.53-3.63 (m, 1 H) 5.96 (br. s., 1 H) 7.91-7.96 (m, 1 H) 8.26-8.31 (m, 1 H).

Description 32: 2-methylfuro[3,4-b]pyridine-5,7-dione (D32)

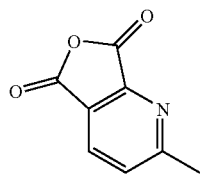

In a 100 ml round-bottomed flask 6-methyl-2,3-pyridinedicarboxylic acid (10 g, 55.2 mmol) and acetic anhydride (26 ml, 276 mmol) were added and heated at 100° C. under nitrogen for 5 hours. After this time the volatiles were removed under vacuum to give the title compound D32 (8.2 g) as a slightly brown solid. $^1$H NMR (400 MHz, DMSO-d$_6$) δ ppm 8.41 (d, 1 H), 7.82 (d, 1 H), 2.73 (s, 3 H).

Description 33: 6-methyl-2-[(methyloxy)carbonyl]-3-pyridinecarboxylic acid (D33)

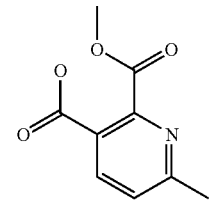

2-methylfuro[3,4-b]pyridine-5,7-dione D32 (3 g) was added portionwise over 5 minutes to stirred MeOH (20 ml) at 0° C. The mixture was stirred at 0° C. for 30 minutes then at room temperature for other 2.5 hours. The solution was evaporated at reduced pressure and the residue recrystallized from toluene (50 ml). The solid was filtered and dried under high vacuum for 30 minutes, obtaining a first batch of the title compound D33 (1.16 g) as pale brown solid. From the toluene solution new solid precipitated. This solid was filtered and dried under high vacuum for 30 minutes, obtaining a second batch of the title compound D33 (352 mg) as pale yellow solid. The toluene solution was then evaporated at reduced pressure and the residue recrystallized again from toluene (25 ml). The solid was filtered and dried under high vacuum for 30 minutes, obtaining a third batch of the title compound D33 (615 mg) as pale yellow solid. UPLC (Basic GEN_QC): rt=0.23 minutes, peak observed: 195 (M+1). $C_9H_9NO_4$ requires 196. $^1$H NMR (400 MHz, DMSO-d$_6$) δ ppm 13.61 (br. s., 1 H), 8.09-8.31 (m, 1 H), 7.51 (m, 1 H), 3.82 (s, 3 H), 2.55 (s, 3 H).

Description 34: methyl 3-({[(1,1-dimethylethyl)oxy]carbonyl}amino)-6-methyl-2-pyridinecarboxylate (D34)

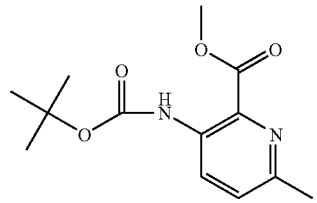

6-methyl-2-[(methyloxy)carbonyl]-3-pyridinecarboxylic acid D33 (1.15 g) was suspended in toluene (40 ml) and DIPEA (1.25 ml, 7.16 mmol) was added, causing the complete dissolution of the solid. This mixture was stirred 10 minutes at room temperature, then diphenyl azidophosphate (1.35 ml, 6.26 mmol) was added in one portion and the mixture was stirred at reflux for 1 hour. The solution was cooled at room temperature and t-BuOH (2.5 ml, 26 mmol) was added in one portion. The mixture was then stirred at 70° C. for 1 hour and then cooled at room temperature, Et$_2$O (50 ml) was added and the resulting solution washed with NaHCO$_3$ saturated solution. The water phases were joined together and back-extracted with Et$_2$O. The two organic solutions were joined together, dried over Na$_2$SO$_4$ and evaporated at reduced pressure, obtaining the crude target material as pale yellow oil. This material was purified by flash chromatography on silica gel (Biotage, EtOAc/Cy from 10/90 to 70/30; Snap-100 g column). The title compound D34 (1.315 g) was obtained as white solid. UPLC (Basic GEN_QC): rt=0.68 minutes, peak observed: 267 (M+1). $C_{13}H_{18}N_2O_4$ requires 266. $^1$H NMR (400 MHz, CDCl$_3$) δ ppm 10.13 (bs., 1 H), 8.77 (d, 1 H), 7.34 (d, 1 H), 4.03 (s, 3H), 2.59 (s, 3 H), 1.53-1.56 (m, 9 H).

Description 35: methyl 3-amino-6-methyl-2-pyridinecarboxylate (D35)

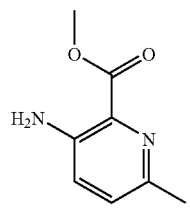

Methyl 3-({[(1,1-dimethylethyl)oxy]carbonyl}amino)-6-methyl-2-pyridinecarboxylate D34 (1.3 g) was dissolved in DCM (80 ml) and the mixture stirred at 0° C. A solution of TFA (5 ml, 64.9 mmol) in DCM (10 ml) was dropped into the cold mixture over 3 minutes. The resulting solution was left under stirring at 0° C. for 30 minutes, then the mixture was left still at room temperature overnight. TFA (4 ml, 51.9 mmol) dissolved in DCM (10 ml) was added over 3 minutes and the mixture stirred again at room temperature for 5 hours. The solution was loaded onto an SCX-25 g column, the column was eluted and after evaporation under reduced pressure of the solvent it was obtained the title compound D35 (770 mg) was obtained as a white solid. UPLC (Basic GEN_QC): rt=0.44 minutes, peak observed: 167 (M+1). $C_8H_{10}N_2O_2$ requires 166. $^1$H NMR (400 MHz, CDCl$_3$) δ ppm 7.14 (d, 1 H), 7.01 (d, 1 H), 3.99 (s, 3 H), 2.52 (s, 3 H).

Description 36: methyl 3-iodo-6-methyl-2-pyridinecarboxylate (D36)

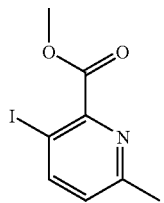

HCl 6 M solution in water (4.5 ml, 27.0 mmol) was added to methyl 3-amino-6-methyl-2-pyridinecarboxylate D35 (768 mg) and the resulting pale yellow mixture was sequentially diluted with water (4×5 ml) and chilled at 0° C. (internal temperature).

A solution of sodium nitrite (480 mg, 6.96 mmol) in water (2 ml) was dropped into the mixture over 1 minute. After this addition the mixture was stirred at 0° C. for 30 minutes, then a solution of KI (1.69 g, 10.18 mmol) in water (2 ml) was added over 1 minute, causing the formation of a dark violet crust (moderate gas evolution). The mixture was left under stirring for 1 hour: during this period the temperature passed from 0° C. to +5° C. EtOAc (50 ml) was then added to the stirred mixture, causing the dissolution of the dark solid. Water (50 ml) and EtOAc (50 ml) were added and the whole mixture was poured into a separator funnel. After the separation of the two phases, the water phase was extracted with EtOAc. All the organic phases were joined together and washed with NaHCO$_3$ saturated solution; the acidic water phase was neutralized by the addition of the previously used NaHCO$_3$ saturated solution and the resulting mixture extracted with EtOAc. All the organic phases were joined together, dried over Na$_2$SO$_4$ and evaporated at reduced pressure, obtaining the crude target material as dark brown/violet oil. This material was purified by silica gel chromatography (Biotage SP4 Snap-100 g column, EtOAc/Cy from 10/90 to 30/70). The title compound D36 was obtained as a pale brown solid (1.1 g). UPLC (Basic GEN_QC): rt=0.68 minutes, peak observed: 278 (M+1). $C_8H_{8I}NO_2$ requires 277. $^1$H NMR (400 MHz, CDCl$_3$) δ ppm 8.12 (d, 1 H), 7.01 (d, 1H), 4.01 (s, 3 H), 2.58 (s, 3 H).

Description D37: methyl 6-methyl-3-(1H-pyrazol-1-yl)-2-pyridinecarboxylate (D37)

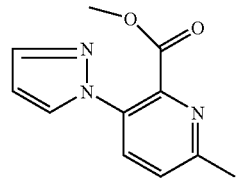

DMF (1.5 ml) was added to a mixture of methyl 3-iodo-6-methyl-2-pyridinecarboxylate D36 (200 mg), 1H-pyrazole (98 mg, 1.444 mmol), (1R,2R)—N,N-dimethyl-1,2-cyclohexanediamine (20.54 mg, 0.144 mmol), bis(copper(I) trifluoromethanesulfonate), benzene complex (18.17 mg, 0.036 mmol) and cesium carbonate (470 mg, 1.444 mmol) in a screw-topped vial. The mixture was degassed via 3 vacuum/nitrogen cycles and heated with shaking to 120° C. for 1 hour. The reaction mixture was evaporated to dryness under reduced pressure. The residue was dissolved in water/MeOH (1:1, 3 ml) and acidified to pH=2 by addition of 4 M HCl solution. The resulting mixture was evaporated to dryness under reduced pressure then the residue was triturated with DCM/MeOH (3:1, 20 ml). The mixture was filtered washing with more DCM/MeOH (3:1, 5 ml). The filtrate was treated with TMS-diazomethane solution (2 M in hexanes, 2 ml, 4 mmol) to re-esterify the acid. The reaction mixture was evaporated under reduced pressure and the residue was purified twice by flash chromatography on silica gel (Biotage Snap 10 g column, EtOAc/Cy from 20/80 to 50/50 and then Biotage KP-NH Snap 11 g column, EtOAc/DCM isocratic 1/99) to give the title compound D37 (107 mg) as a colourless gum.

UPLC (Basic QC_POS_50-800): rt=0.51 minutes, peak observed: 218 (M+1). $C_{11}H_{11}N_3O_2$ requires 217. $^1$H NMR (400 MHz, CDCl$_3$) δ ppm 7.63-7.86 (m, 3 H), 7.39 (m, 1 H), 6.48 (m, 1 H), 3.85 (s, 3 H), 2.68 (s, 3 H).

Description D38: 6-methyl-3-(1H-pyrazol-1-yl)-2-pyridinecarboxylic acid (D38)

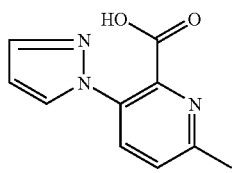

A solution of methyl 6-methyl-3-(1H-pyrazol-1-yl)-2-pyridinecarboxylate D37 (106 mg) and LiOH (17.53 mg, 0.732 mmol) in THF/water (2:1, 6 ml) was stirred overnight. The mixture was evaporated under reduced pressure; the residue was taken up in water (2 ml) and the pH was adjusted to pH=2 with 1 M HCl solution. The mixture was loaded onto a pre-conditioned C18 column (5 g, eluted with water and then MeOH). The methanol fractions were evaporated under reduced pressure to give the title compound D38 (98 mg) as a white solid.

UPLC (Basic QC_POS_50-800): rt=0.30 minutes, peak observed: 160 [(M−CO$_2$)+1]. C$_{10}$H$_9$N$_3$O$_2$ requires 203. $^1$H NMR (400 MHz, methanol-d$_4$) δ ppm 7.77-8.03 (m, 2 H), 7.74 (m, 1 H), 7.58 (m, 1 H), 6.55 (m, 1 H), 2.66 (s, 3 H).

Description 39: methyl 6-methyl-3-(2H-1,2,3-triazol-2-yl)-2-pyridinecarboxylate (D39)

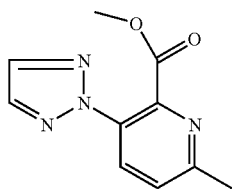

DMF (1.5 ml) was added to a mixture of methyl 3-iodo-6-methyl-2-pyridinecarboxylate D36 (100 mg), 1H-1,2,3-triazole (49.9 mg, 0.722 mmol), (1R,2R)—N,N'-dimethyl-1,2-cyclohexanediamine (10.27 mg, 0.072 mmol), CuI (3.44 mg, 0.018 mmol) and Cs$_2$CO$_3$ carbonate (235 mg, 0.722 mmol) in a microwave vial. The mixture was degassed via three vacuum/nitrogen cycles then irradiated in a single mode microwave reactor to 120° C. for 20 minutes. The mixture was irradiated in a single mode microwave reactor to 120° C. for a further 40 minutes. The reaction mixture was cooled and filtered washing the solids with EtOAc. The solids were dissolved in pH=3 buffer solution (5 ml); UPLC check of this aqueous solution showed it contained a considerable quantity of 6-methyl-3-(2H-1,2,3-triazol-2-yl)-2-pyridinecarboxylic acid. The aqueous phase was extracted repeatedly with DCM; the combined DCM extracts were diluted with MeOH (50 ml) and treated with TMS-diazomethane. The volatiles were evaporated to give a yellow residue that was purified by flash chromatography on silica gel (Biotage, SNAP 10 g column, 10%-50% EtOAc/Cy) to give the title compound D39 (38 mg) as a white solid. UPLC (Basic QC_POS_50-800): rt=0.57 minutes, peak observed: 219 (M+1). C$_{10}$H$_{10}$N$_4$O$_2$ requires 218. $^1$H NMR (400 MHz, CDCl$_3$) δ ppm 8.20 (d, 1 H), 7.87 (s, 2 H), 7.44 (d, 1 H), 3.94 (s, 3 H), 2.71 (s, 3 H).

Description 40: 6-methyl-3-(2H-1,2,3-triazol-2-yl)-2-pyridinecarboxylic acid (D40)

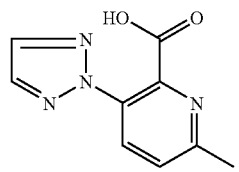

A solution of methyl 6-methyl-3-(2H-1,2,3-triazol-2-yl)-2-pyridinecarboxylate D39 (36 mg) and LiOH (5.93 mg, 0.247 mmol) in THF/water (2:1, 3 ml) was stirred overnight. The mixture was evaporated under reduced pressure; the residue was taken up in water (2 ml) and neutralised with 1 M HCl water solution and then loaded onto a pre-conditioned C18 5 g column (the column was eluted with water and then MeOH). The methanol fractions were evaporated under reduced pressure to give the title compound D40 (34 mg) as a white solid. UPLC (Basic QC_POS_50-800): rt=0.30 minutes. peak observed: 205 (M+1). C$_9$H$_8$N$_4$O$_2$ requires 204. $^1$H NMR (400 MHz, MeOD) δ (ppm) 8.24 (d, 1 H), 7.99 (s, 2 H), 7.61 (d, 1 H), 2.67 (s, 3 H).

EXAMPLES

In the following Examples the relative stereochemistry of the compounds is derived from the stereochemistry of the previous intermediates from which the compounds were synthesised. In some Examples the relative stereochemistry has been confirmed on the final compounds as well. The final compounds are present as a mixture of conformers of variable ratio according to the specific Example. For Example E1 is assigned the SYN relative stereochemistry derived from the stereochemistry of the previous intermediate D8. The product is present as a mixture of conformers.

Example 1

N-[((1S,4S,6S)-3-{[6-Methyl-3-(propyloxy)-2-pyridinyl]carbonyl}-3-azabicyclo[4.1.0]hept-4-yl)methyl]-5-(trifluoromethyl)-2-pyridinamine hydrochloride (E1)

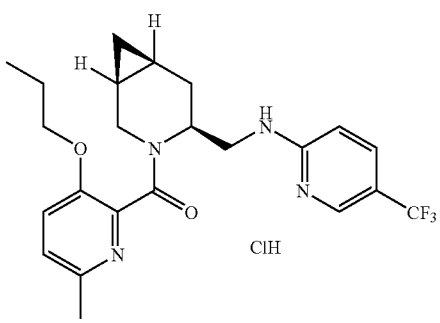

To a solution of 6-methyl-3-(propyloxy)-2-pyridinecarboxylic acid D16 (0.0215 g) in DMF (1.5 ml) was added TBTU (0.0497 g, 0.155 mmol) and DIPEA (0.116 ml, 0.664 mmol) and the resulting mixture was stirred for 30 minutes.

To that solution was added a solution of N-[(1S,4S,6S)-3-azabicyclo[4.1.0]hept-4-ylmethyl]-5-(trifluoromethyl)-2-pyridinamine D12 (0.030 g) in DMF (0.5 ml) and stirred for 1.5 hours. EtOAc (5 ml) and NaHCO$_3$ aqueous saturated solution (10 ml) were added and the aqueous phase was extracted with EtOAc. After the separation the organic layer was passed through a phase separator cartridge and then evaporated under reduced pressure. The brown oil obtained was purified via Biotage SP4 (NH 12+M column; Cy/EtOAc, 1/0 to 7/3 5 CV, 7/3 20 CV). Collected and evaporated fractions gave N-[((1S,4S,6S)-3-{[6-methyl-3-(propyloxy)-2-pyridinyl]carbonyl}-3-azabicyclo[4.1.0]hept-4-yl)methyl]-5-(trifluoromethyl)-2-pyridinamine free base of the title compound E1 (0.038 g) as white solid. HPLC (walk-up): rt=4.46 min MS: (ES/+) m/z 449 (M+1). C$_{23}$H$_{27}$F$_3$N$_4$O$_2$ requires 448. $^1$H NMR [the SYN relative stereochemistry is derived from the stereochemistry of the previous intermediate D8. The product is present as a mixture of conformers. The assignment is provided for the major component]

$^1$H NMR (500 MHz, DMSO-d$_6$) δ ppm 8.24-8.31 (m, 1 H), 7.61-7.73 (m, 1 H), 7.15-7.48 (m, 3 H), 6.60-6.88 (m, 1 H), 4.06-4.25 (m, 1 H), 3.89-3.97 (m, 2 H), 3.57-3.64 (m, 1 H), 3.35-3.43 (m, 2 H), 2.56-2.66 (m, 1 H), 2.40 (s, 3 H), 2.33-2.43 (m, 1 H), 1.54-1.67 (m, 2 H), 1.00-1.24 (m, 2 H), 0.88 (t, 3 H), 0.80-0.86 (m, 1 H), 0.61-0.69 (m, 1 H), 0.16-0.23 (m, 1 H).

To a solution of N-[((1S,4S,6S)-3-{[6-methyl-3-(propyloxy)-2-pyridinyl]carbonyl}-3-azabicyclo[4.1.0]hept-4-yl)methyl]-5-(trifluoromethyl)-2-pyridinamine (0.036 g) in DCM (1 ml) was added HCl (1 M in Et$_2$O) (0.161 ml, 0.161 mmol) and stirred for 30 minutes. The solvents were removed under reduced pressure to give a yellowish solid, which was triturated with Et$_2$O (3×1 ml). The solvent was removed by suction and the residue was dried under vacuum at 40° C. overnight to yield the title compound E1 (0.038 g) as white solid. HPLC (walk-up): rt=4.48 min MS: (ES/+) m/z: 449 (M+1−HCl). C$_{23}$H$_{27}$F$_3$N$_4$O$_2$HCl requires 484. $^1$H NMR (400 MHz, DMSO-d$_6$) δ ppm 8.29-8.45 (m, 1 H), 7.77-7.89 (m, 1 H), 7.58-7.66 (m, 2 H), 7.33-7.42 (m, 1 H), 6.85-7.04 (m, 1 H), 4.13-4.21 (m, 1 H), 3.95-4.02 (m, 2 H), 3.37-3.70 (m, 3 H), 2.60-2.74 (m, 1 H), 2.38-2.48 (m, 4 H), 1.56-1.73 (m, 2 H), 1.02-1.32 (m, 2 H), 0.82-0.96 (m, 4 H), 0.64-0.73 (m, 1 H), 0.20-0.28 (m, 1 H).

Example 2

N-[((1S,4S,6S)-3-{[3-(Ethyloxy)-6-methyl-2-pyridinyl]carbonyl}-3-azabicyclo[4.1.0]hept-4-yl)methyl]-5-(trifluoromethyl)-2-pyridinamine (E2):

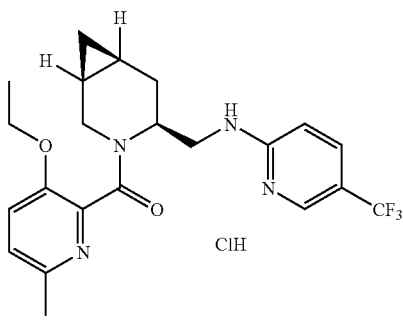

Following a similar procedure to that described for Example 1, N-[(1S,4S,6S)-3-azabicyclo[4.1.0]hept-4-ylmethyl]-5-(trifluoromethyl)-2-pyridinamine D12 (0.030 g) and 3-(ethyloxy)-6-methyl-2-pyridinecarboxylic acid D15 (0.020 g) were reacted to give the free base of the title compound (0.044 g, 0.101 mmol, 92% yield). HPLC (walk-up): rt=4.14 min. MS: m/z (ES/+): 435 (M+1). C$_{22}$H$_{25}$F$_3$N$_4$O$_2$ requires 434. $^1$H NMR [the SYN relative stereochemistry is derived from the stereochemistry of the previous intermediate D8. The product is present as a mixture of conformers. The assignment is provided for the major component] (400 MHz, DMSO-d$_6$) δ ppm: 8.26 (m, 1 H), 7.72-7.56 (m, 1 H), 7.18-7.47 (m, 3H), 6.83-6.61 (m, 1 H), 4.24-4.10 (m, 1 H), 4.10-3.88 (m, 2 H), 3.67-3.34 (m, 3 H), 2.67-2.56 (m, 1 H), 2.43-2.37 (s, 3 H), 2.43-2.34 (m, 1 H), 1.23-1.19 (m, 3 H), 1.20-0.8 (m, 3 H), 0.72-0.58 (m, 1 H), 0.15-0.24 (m, 1 H).

Following a similar procedure to that described for Example 1, starting from the free base N-[((1S,4S,6S)-3-{[3-(ethyloxy)-6-methyl-2-pyridinyl]carbonyl}-3-azabicyclo[4.1.0]hept-4-yl)methyl]-5-(trifluoromethyl)-2-pyridinamine (0.0415 g) was obtained the title compound E2 (0.045 g). HPLC (walk-up): rt=4.16 min MS: m/z (ES/+): 435 (M+1−HCl). C$_{22}$H$_{25}$F$_3$N$_4$O$_2$.HCl requires 470. $^1$H NMR (400 MHz, DMSO-d$_6$) δ ppm: 8.5-6.0 (m, 6 H), 5.0-2.5 (m, 7 H), 2.5-0.0 (m, 12 H).

Example 3

N-[((1S,4S,6S)-3-{[6-Methyl-3-(2-pyrimidinyl)-2-pyridinyl]carbonyl}-3-azabicyclo[4.1.0]hept-4-yl)methyl]-5-(trifluoromethyl)-2-pyridinamine (E3)

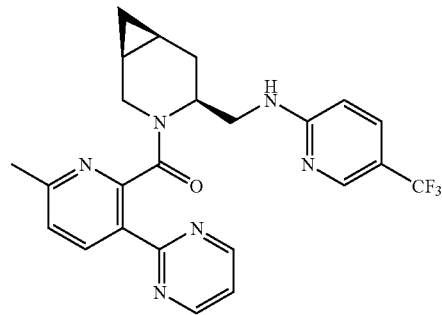

To a solution of 6-methyl-3-(2-pyrimidinyl)-2-pyridinecarboxylic acid D19 (99 mg), DIPEA (0.066 ml, 0.376 mmol) and N-[(1S,4S,6S)-3-azabicyclo[4.1.0]hept-4-ylmethyl]-5-(trifluoromethyl)-2-pyridinamine D12 (34 mg) in DCM (3 ml), stirred under nitrogen at room temperature was added TBTU (60.4 mg, 0.188 mmol) in one charge. The reaction mixture was stirred at room temperature for 5 hours. NaHCO$_3$ aqueous saturated solution was added and the aqueous extracted with DCM, the phases were separated on a hydrophobic frit and the combined organic solvent was removed to give the crude product which was purified by flash chromatography (silica —NH 11 g column, gradient elution from Cy to Cy/EtOAc 2:8 in 30 minutes, flow rate 30 mls/minute). The product so obtained was purified a second time by flash chromatography (silica —NH 11 g column gradient elution from Cy to Cy/EtOAc 1:1 in 20 minutes, flow rate 30 mls/minute) to afford the title compound E3 (21 mg). UPLC (Acid GEN_QC): rt1=0.68 minutes, peak observed: 469 (M+1). C$_{24}$H$_{23}$F$_3$N$_6$O requires 460. $^1$H NMR (500 MHz, CDCl$_3$) δ ppm 0.08-0.16 (m, 1 H), 0.73-0.81 (m, 1 H), 0.82-1.32 (m, 3H), 2.46-2.58 (m, 2 H), 2.66 (s, 3 H), 3.52-3.69 (m, 2 H), 3.70-3.80 (m, 1 H), 4.47-4.66 (m, 1 H), 6.38-6.50 (m, 1

H), 6.74-7.01 (m, 1 H), 7.08 (t, 1 H), 7.35 (d, 1 H), 7.47 (d, 1 H), 8.33 (s, 1 H), 8.54-8.64 (m, 3 H).

Example 4

N-[((1S,4S,6S)-3-{[6-methyl-3-(2-pyrimidinyl)-2-pyridinyl]carbonyl}-3-azabicyclo[4.1.0]hept-4-yl)methyl]-5-(trifluoromethyl)-2-pyrazinamine (E4)

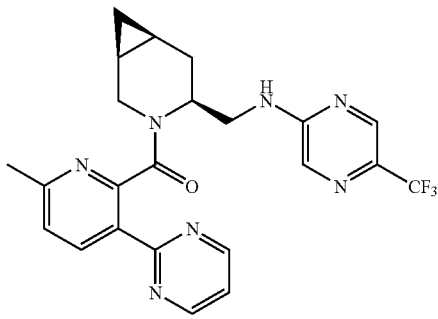

To a solution of 6-methyl-3-(2-pyrimidinyl)-2-pyridinecarboxylic acid D19 (66.2 mg) in dry DCM (0.5 ml) at room temperature DIPEA (0.038 ml, 0.220 mmol) was added followed by TBTU (38.9 mg, 0.121 mmol). The mixture dissolved completely in about 10 minutes. After 30 minutes N-[(1S,4S,6S)-3-azabicyclo[4.1.0]hept-4-ylmethyl]-5-(trifluoromethyl)-2-pyrazinamine D31 (30 mg) dissolved in dry DCM (0.5 ml) was added dropwise. The reaction mixture was left reacting for 16 hours. The reaction mixture was taken up with DCM (10 mls) and NaHCO$_3$ saturated solution (15 mls). The aqueous layer was back extracted with DCM (2×10 mls). The combined organic layers were washed with brine (1×10 mls). The organic was dried Na$_2$SO$_4$, filtered and concentrated to get crude material. The crude product was purified by silica —NH chromatography (Biotage SP—column size 11 g, using EtOAc 100% as eluent). The product recovered was not pure so it was purified again by C18 Phase [Snap 60 g, eluting with water (HCOOH 0.5%): Acetonitrile (HCOOH 0.5%)=95:5 to 5:95]. It was recovered the title compound E4 (25 mg). UPLC: (Acid Final_QC): rt=0.86 minutes, peaks observed: 470 (M+1). C$_{23}$H$_{22}$F$_3$N$_7$O requires 469. $^1$H NMR (400 MHz, DMSO-d$_6$) δ ppm 8.86-8.79 (m, 2 H), 8.51-8.47 (m, 1 H), 8.41-8.37 (m, 1 H), 8.13-7.81 (m, 2 H), 7.52-7.38 (m, 2 H) 4.24-4.12 (m, 1 H) 3.82-3.66 (m, 2 H), 3.64-3.55 (m, 1 H), 2.69 (s, 3 H), 2.68-2.61 (m, 1 H), 2.46-2.39 (m, 1 H), 1.20-1.02 (m, 2 H), 0.99-0.89 (m, 1 H), 0.68-0.59 (m, 1 H), 0.23-0.16 (m, 1 H).

Example 5

N-[((1S,4S,6S)-3-{[6-methyl-3-(1H-pyrazol-1-yl)-2-pyridinyl]carbonyl}-3-azabicyclo[4.1.0]hept-4-yl)methyl]-5-(trifluoromethyl)-2-pyrazinamine (E5)

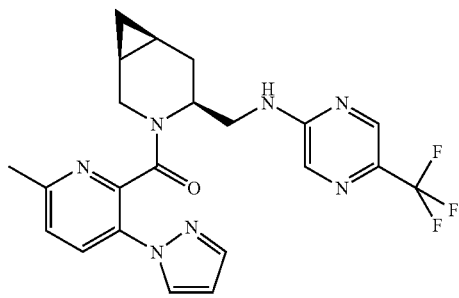

6-methyl-3-(1H-pyrazol-1-yl)-2-pyridinecarboxylic acid D38 (24.63 mg) was dissolved in 1 ml of DMF, then TBTU (46.0 mg, 0.143 mmol) and DIPEA (0.025 ml, 0.143 mmol) were added. The suspension was stirred for 30 minutes at room temperature. N-[(1S,4S,6S)-3-azabicyclo[4.1.0]hept-4-ylmethyl]-5-(trifluoromethyl)-2-pyrazinamine D31 (30 mg) dissolved in 1 ml of DMF was added and the reaction was stirred overnight at room temperature. NaHCO$_3$ saturated solution were added, and the aqueous layer was extracted with of DCM. The organic layers were collected together, dried through a phase separator and concentrated under vacuum to give a crude which was purified by SCX chromatography (column size 5 g). A second purification was performed by silica —NH chromatography (Biotage SP—column size 11 g, using Cy:EtOAc=5:5 to EtOAc). It was recovered the title compound E5 (22 mg). UPLC: (Acid Final_QC): rt=0.81 and 0.85 minutes (rotamers present), peaks observed: 458 (M+1). C$_{22}$H$_{22}$F$_3$N$_7$O requires 457. $^1$H NMR (400 MHz, CDCl$_3$) δ ppm 8.29 (s, 1 H), 7.85-7.77 (m, 3 H), 7.52 (s, 1 H), 7.38-7.32 (m, 1 H), 7.05-6.89 (m, 1 H) 6.35-6.30 (m, 1 H) 4.58-4.37 (m, 1 H), 3.77-3.66 (m, 1 H), 3.65-3.37 (m, 2 H), 2.65 (s, 3 H), 2.50-2.36 (m, 2 H), 1.42-0.83 (m, 3 H), 0.82-0.71 (m, 1 H), 0.15-0.06 (m, 1 H).

Example 6

N-[((1S,4S,6S)-3-{[6-methyl-3-(2H-1,2,3-triazol-2-yl)-2-pyridinyl]carbonyl}-3-azabicyclo[4.1.0]hept-4-yl)methyl]-5-(trifluoromethyl)-2-pyrazinamine (E6)

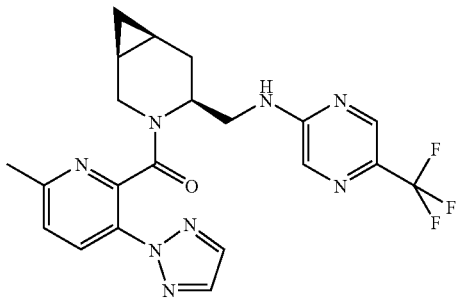

6-methyl-3-(2H-1,2,3-triazol-2-yl)-2-pyridinecarboxylic acid D40 (33.0 mg) was dissolved in 1 ml of DCM, then TBTU (61.3 mg, 0.191 mmol) and DIPEA (0.033 ml, 0.191 mmol) were added. The suspension was stirred for 30 minutes at room temperature. N-[(1S,4S,6S)-3-azabicyclo[4.1.0]hept-4-ylmethyl]-5-(trifluoromethyl)-2-pyrazinamine D31 (40 mg) dissolved in 1 ml of DCM was added and the reaction was stirred overnight at room temperature. 3 ml of NaHCO$_3$ saturated solution were added, and the aqueous layer was extracted with DCM. The organic layers were collected together, dried through a phase separator and concentrated under vacuum to give a crude which was purified by SCX chromatography (column size 5 g). A second purification was performed by Silica —NH chromatography (Biotage SP—column size 25 g, using Cy:EtOAc=5:5 to EtOAc). It was recovered the title compound E6 (30 mg). UPLC: (Acid Final_QC): rt=0.76 and 0.80 minutes (rotamers present), peaks observed: 459 (M+1). C$_{21}$H$_{21}$F$_3$N$_8$O requires 458. $^1$H NMR (400 MHz, DMSO-d$_6$) δ ppm 8.38 (s, 1 H) 8.28-8.22 (m, 1 H) 8.08-8.06 (s, 2 H), 7.90-7.78 (m, 2 H), 7.57-7.51 (m, 1 H) 4.20-4.08 (m, 1 H) 3.76-3.40 (m, 3 H), 2.68-2.61 (m, 1 H), 2.56 (s, 3 H), 2.44-2.35 (m, 1 H), 1.28-0.95 (m, 2 H), 0.92-0.83 (m, 1 H), 0.68-0.60 (m, 1 H), 0.24-0.18 (m, 1 H).

Example 7

Determination of Antagonist Affinity at Human Orexin-1 and 2 Receptors Using FLIPR Cell Culture Adherent Chinese Hamster Ovary (CHO) cells, stably expressing the recombinant human Orexin-1 or human Orexin-2 receptors or Rat Basophilic Leukaemia Cells (RBL) stably expressing recombinant rat Orexin-1 or rat Orexin-2 receptors were maintained in culture in Alpha Minimum Essential Medium (Gibco/Invitrogen, cat. no.; 22571-020), supplemented with 10% decomplemented foetal bovine serum (Life Technologies, cat. no. 10106-078) and 400 µg/mL Geneticin G418 (Calbiochem, cat. no. 345810). Cells were grown as monolayers under 95%:5% air:$CO_2$ at 37° C.

The sequences of the human orexin 1, human orexin 2, rat orexin 1 and rat orexin 2 receptors used to test the compounds of examples 1 and 2 were as published in Sakurai, T. et al (1998) Cell, 92 pp 573 to 585, with the exception that the human orexin 1 receptor sequence used had the amino acid residue alanine at position 280 and not glycine as reported in Sakurai et al. The sequences of the receptors used to test the compounds of examples 3 to 6 were the same as above with the exception that the orexin 1 receptor sequence was identical to that published in Sakurai supra.

Measurement of $[Ca^{2+}]_i$ Using the FLIPR™

Cells were seeded into black clear-bottom 384-well plates (density of 20,000 cells per well) in culture medium as described above and maintained overnight (95%:5% air:$CO_2$ at 37° C.). On the day of the experiment, culture medium were discarded and the cells washed three times with standard buffer (NaCl, 145 mM; KCl, 5 mM; HEPES, 20 mM; Glucose, 5.5 mM; $MgCl_2$, 1 mM; $CaCl_2$, 2 mM) added with Probenecid 2.5 mM. The plates were then incubated at 37° C. for 60 minutes in the dark with 2 µM FLUO-4AM dye to allow cell uptake of the FLUO-4AM, which is subsequently converted by intracellular esterases to FLUO-4, which is unable to leave the cells. After incubation, cells were washed three times with standard buffer to remove extracellular dye and 30 pit of buffer were left in each well after washing.

Compounds of the invention were tested in a final assay concentration range from $1.66 \times 10^{-5}$M to $1.58 \times 10^{-11}$M. Compounds of the invention were dissolved in dimethylsulfoxide (DMSO) at a stock concentration of 10 mM. These stock solutions were serially diluted with DMSO and 1 µL of each dilution was transferred to a 384 well compound plate. Immediately before introducing compound to the cells, buffer solution (50 µl/well) was added to this plate. To allow agonist stimulation of the cells, a stock plate containing a solution of human orexin A (hOrexin A) was diluted with buffer to final concentration just before use. This final concentration of hOrexin A was equivalent to the calculated EC80 for hOrexinA agonist potency in this test system. This value was obtained by testing hOrexinA in concentration response curve (at least 16 replicates) the same day of the experiment.

The loaded cells were then incubated for 10 min at 37° C. with test compound. The plates were then placed into a FLIPR™ (Molecular Devices, UK) to monitor cell fluorescence ($\lambda_{ex}$=488 nm, $\lambda_{EM}$=540 nm) (Sullivan E, Tucker E M, Dale I L. Measurement of $[Ca^{2+}]_i$ using the fluometric imaging plate reader (FLIPR). In: Lambert D G (ed.), *Calcium Signaling Protocols*. New Jersey: Humana Press, 1999, 125-136). A baseline fluorescence reading was taken over a 5 to 10 second period, and then 10 µL of EC80 hOrexinA solution was added. The fluorescence was then read over a 4-5 minute period.

Data Analysis

Functional responses using FLIPR were measured as peak fluorescence intensity minus basal fluorescence and expressed as a percentage of a non-inhibited Orexin-A-induced response on the same plate. Iterative curve-fitting and parameter estimations were carried out using a four parameter logistic model and Microsoft Excel (Bowen W P, Jerman J C. Nonlinear regression using spreadsheets. *Trends Pharmacol. Sci.* 1995; 16: 413-417). Antagonist affinity values ($IC_{50}$) were converted to functional $pK_i$ values using a modified Cheng-Prusoff correction (Cheng Y C, Prusoff W H. Relationship between the inhibition constant (1c) and the concentration of inhibitor which causes 50 percent inhibition ($IC_{50}$) of an enzymatic reaction. *Biochem. Pharmacol.* 1973, 22: 3099-3108).

$$fpKi = -\log \frac{(IC_{50})}{\left(2 + \left(\frac{[agonist]}{(EC_{50})}\right)^n\right)^{1/n} - 1}$$

Where [agonist] is the agonist concentration, $EC_{50}$ is the concentration of agonist giving 50% activity derived from the agonist dose response curve and n=slope of the dose response curve. When n=1 the equation collapses to the more familiar Cheng-Prusoff equation.

Compounds of examples 1 to 6 were tested according to the method of example 7. All compounds gave fpKi values from 8.6 to 9.5 at the human cloned orexin-1 receptor and from 7.5 to 9.3 at the human cloned orexin-2 receptor.

The invention claimed is:

1. A compound of formula (I)

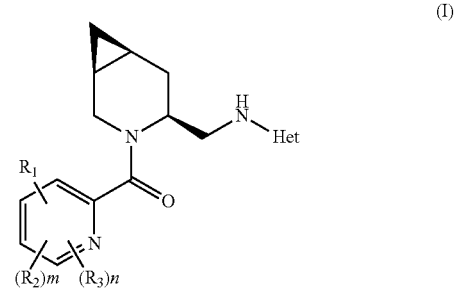

where:
- Het is a heteroaryl group selected from the group consisting of pyridinyl, pyrimidinyl, pyridazinyl or pyrazinyl, said heteroaryl group being optionally substituted with 1, 2 or 3 substituents independently selected from the group consisting of: $C_{1-4}$alkyl, halo, $C_{1-4}$alkoxy, halo$C_{1-4}$alkyl, halo$C_{1-4}$alkoxy and cyano;
- $R_1$ is $C_{1-4}$alkyl, halo, $C_{1-4}$alkoxy, halo$C_{1-4}$alkyl, halo$C_{1-4}$alkoxy, cyano, $C_{1-4}$alkyl$SO_2$, $C_{3-8}$ cycloalkyl$SO_2$, $C_{3-8}$cycloalkyl$CH_2SO_2$, phenyl or a 5 or 6 membered heterocyclyl group containing 1, 2 or 3 atoms selected from N, O or S, which phenyl or heterocyclyl group is optionally substituted with $C_{1-4}$alkyl, halo, $C_{1-4}$alkoxy, halo$C_{1-4}$alkyl, halo$C_{1-4}$alkoxy or cyano;
- $R_2$ is $C_{1-4}$alkyl, halo, $C_{1-4}$alkoxy, halo$C_{1-4}$alkyl, halo$C_{1-4}$alkoxy, cyano, phenyl or a 5 or 6 membered heterocyclyl group containing 1, 2 or 3 atoms selected from N, O or S, which phenyl or heterocyclyl group is optionally substituted with $C_{1-4}$alkyl, halo, $C_{1-4}$alkoxy, halo$C_{1-4}$ alkyl, halo$C_{1-4}$alkoxy or cyano;
- $R_3$ is $C_{1-4}$alkyl, halo, $C_{1-4}$alkoxy, halo$C_{1-4}$alkyl, halo$C_{1-4}$alkoxy or cyano;
- m is 0 or 1; and
- n is 0 or 1;

or a pharmaceutically acceptable salt thereof.

2. The compound or salt according to claim 1, where Het is pyrimidinyl.

3. The compound or salt according to claim 1, where m is 0 and n is 0.

4. The compound or salt according to claim 1, where m is 1 and n is 0.

5. The compound or salt according to claim 1, where $R_1$ is $CH_3$.

6. The compound or salt according to claim 1, where Het is pyridinyl substituted with trifluoromethyl, m is 1, n is 0, $R_1$ is $CH_3$ and $R_2$ is pyrimidinyl.

7. The compound or salt according to claim 1, where Het is pyrazinyl substituted with trifluoromethyl, m is 1, n is 0, $R_1$ is $CH_3$ and $R_2$ is pyrimidinyl.

8. The compound or salt according to claim 1, where Het is substituted with halo$C_{1-4}$alkyl.

9. The compound or salt according to claim 8, where Het is substituted with trifluoromethyl.

10. The compound or salt according to claim 1, where Het is pyridinyl.

11. The compound or salt according to claim 10, where Het is pyridinyl substituted with trifluoromethyl or cyano.

12. The compound or salt according to claim 1, where $R_2$ is methoxy, ethoxy, propoxy, phenyl, pyrimidinyl, oxadiazolyl, oxazolyl, isoxazolyl, thiazolyl, triazolyl, imidazolyl, pyrazolinyl, pyridazinyl, pyrazinyl or pyridinyl.

13. The compound or salt according to claim 12, where $R_2$ is pyrimidinyl.

14. A pharmaceutical composition comprising the compound or salt according to claim 1 and one or more pharmaceutically acceptable carriers.

15. A compound selected from the group consisting of:
N-[((1S,4S,6S)-3-{[6-methyl-3-(propyloxy)-2-pyridinyl]carbonyl}-3-azabicyclo[4.1.0]hept-4-yl)methyl]-5-(trifluoromethyl)-2-pyridinamine;
N-[((1S,4S,6S)-3-{[3-(ethyloxy)-6-methyl-2-pyridinyl]carbonyl}-3-azabicyclo [4.1.0]hept-4-yl)methyl]-5-(trifluoromethyl)-2-pyridinamine;
N-[((1S,4S,6S)-3-{[6-methyl-3-(2-pyrimidinyl)-2-pyridinyl]carbonyl}-3-azabicyclo[4.1.0]hept-4-yl)methyl]-5-(trifluoromethyl)-2-pyridinamine;
N-[((1S,4S,6S)-3-{[6-methyl-3-(2-pyrimidinyl)-2-pyridinyl]carbonyl}-3-azabicyclo[4.1.0]hept-4-yl)methyl]-5-(trifluoromethyl)-2-pyrazinamine;
N-[((1S,4S,6S)-3-{[6-methyl-3-(1H-pyrazol-1-yl)-2-pyridinyl]carbonyl}-3-azabicyclo[4.1.0]hept-4-yl)methyl]-5-(trifluoromethyl)-2-pyrazinamine; and
N-[((1S,4S,6S)-3-{[6-methyl-3-(2H-1,2,3-triazol-2-yl)-2-pyridinyl]carbonyl}-3-azabicyclo[4.1.0]hept-4-yl)methyl]-5-(trifluoromethyl)-2-pyrazinamine;
or a pharmaceutically acceptable salt thereof.

16. A pharmaceutical composition comprising the compound or salt according to claim 15 and one or more pharmaceutically acceptable carriers.

* * * * *